US011243207B2

(12) United States Patent
Copland, III et al.

(10) Patent No.: US 11,243,207 B2
(45) Date of Patent: Feb. 8, 2022

(54) ASSESSING AND TREATING CANCER

(71) Applicant: Mayo Foundation for Medical Education and Research, Rochester, MN (US)

(72) Inventors: John A. Copland, III, Ponte Vedra Beach, FL (US); Laura Ann Marlow, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/368,477

(22) Filed: Mar. 28, 2019

(65) Prior Publication Data
US 2019/0302121 A1 Oct. 3, 2019

Related U.S. Application Data

(60) Provisional application No. 62/650,217, filed on Mar. 29, 2018.

(51) Int. Cl.
*G01N 33/574* (2006.01)
*A61K 31/4412* (2006.01)
*A61P 35/00* (2006.01)

(52) U.S. Cl.
CPC ... *G01N 33/57438* (2013.01); *A61K 31/4412* (2013.01); *A61P 35/00* (2018.01); *G01N 33/57484* (2013.01)

(58) Field of Classification Search
None
See application file for complete search history.

(56) References Cited

U.S. PATENT DOCUMENTS

| | | | |
|---|---|---|---|
| 6,066,730 A | 5/2000 | Adams et al. | |
| 6,297,217 B1 | 10/2001 | Adams et al. | |
| 6,548,668 B2 | 4/2003 | Adams et al. | |
| 6,699,835 B2 | 3/2004 | Plamondon et al. | |
| 7,014,866 B2 | 3/2006 | Infeld et al. | |
| 7,109,323 B2 | 9/2006 | Plamondon et al. | |
| 7,531,526 B2 | 5/2009 | Adams et al. | |
| 7,687,456 B2 | 3/2010 | Zhou et al. | |
| 7,691,852 B2 | 4/2010 | Shenk et al. | |
| 8,080,545 B2 | 12/2011 | Shenk et al. | |
| 8,080,576 B2 | 12/2011 | Shenk et al. | |
| 8,088,741 B2 | 1/2012 | Smyth et al. | |
| 8,357,683 B2 | 1/2013 | Shenk et al. | |
| 8,431,571 B2 | 4/2013 | Shenk et al. | |
| 9,233,102 B2 | 1/2016 | Copland, III et al. | |
| 2006/0079502 A1 | 4/2006 | Lang | |
| 2006/0094744 A1 | 5/2006 | Maryanoff et al. | |
| 2013/0096181 A1 | 4/2013 | Ashkenazi et al. | |
| 2016/0000673 A1 | 3/2016 | Fand et al. | |
| 2017/0015654 A1 | 1/2017 | Imamura et al. | |
| 2019/0345123 A1 | 11/2019 | Copland, III | |
| 2020/0061055 A1 | 2/2020 | Von Roemeling | |

FOREIGN PATENT DOCUMENTS

| | | |
|---|---|---|
| WO | WO 2003/006009 | 1/2003 |
| WO | WO 2008/120759 | 10/2008 |
| WO | WO 2009/020448 | 2/2009 |
| WO | WO 2009/051581 | 4/2009 |
| WO | WO 2009/154737 | 12/2009 |
| WO | WO 2010/036357 | 4/2010 |
| WO | WO 2011/123502 | 10/2011 |
| WO | WO 2012/151451 | 11/2012 |
| WO | WO 2014/153150 | 9/2014 |
| WO | WO 2016/022955 | 2/2016 |
| WO | WO 2016/141299 | 9/2016 |
| WO | WO 2016/183326 | 11/2016 |

OTHER PUBLICATIONS

Ma et al., "Stearoyl-CoA desaturase regulates sorafenib resistance via modulation of ER stress-induced differentiation", Journal of Hepatology, 2017, vol. 67, No. 5, pp. 979-990 (Year: 2017).*
Ma et al., "Stearoyl-CoA Desaturase (SCD1) regulates liver tumor initiating cells through modulating ER stress [Abstract]", Cancer Res., 2017, vol. 77, supplement 13, Abstract 4772 (Year: 2017).*
Chen et al, "Targeting oncogenic Myc as a strategy for cancer treatment", Signal Transduction and Targeted Therapy, 2018 (published online Feb. 23, 2018), vol. 3, No. 5, pp. 1-7 (Year: 2018).*
Ackerman and Simon, "Hypoxia, lipids, and cancer: surviving the harsh tumor microenvironment," Trends Cell Biol., 24(8):472-8, Aug. 2014.
Ahn, "An evaluation of phase I cancer clinical trial designs," Stat. Med., 17(14):1537-49, Jul. 1998.
Angelucci et al., "Stearoyl-CoA desaturase 1 and paracrine diffusible signals have a major role in the promotion of breast cancer cell migration induced by cancer-associated fibroblasts," Br. J. Cancer. 112(10):1675-86, Apr. 2015.
Aparicio et al., "Examining the utility of patient-derived xenograft mouse models," Nat. Rev. Cancer, 15(5):311-6, Apr. 2015.
Bankaitis, "Unsaturated fatty acid-induced non-canonical autophagy: unusual? or unappreciated?" EMBO J., 34(8):978-80, Apr. 2015.
Bansal et al., "Stearoyl-CoA desaturase plays an important role in proliferation and chemoresistance in human hepatocellular carcinoma," J. Surg. Res., 186(1):29-38, Jan. 2014.
Ben-David et al., "Selective Elimination of Human Pluripotent Stem Cells by an Oleate Synthesis Inhibitor Discovered in a High-Throughput Screen," Cell Stem Cell, 12(2):167-79, Feb. 2013.
Berge et al., "Pharmaceutical Salts", J Pharm Sci., 66(1):1-19, Jan. 1977.
Böhm et al., "Scaffold hopping," Drug Discovery Today: Technologies., 1(3):217-224, 2004.

(Continued)

*Primary Examiner* — Jeffrey S Lundgren
*Assistant Examiner* — Michael J Schmitt
(74) *Attorney, Agent, or Firm* — Fish & Richardson P.C.

(57) ABSTRACT

This document relates to methods and materials for identifying and/or treating mammals having cancer (e.g., a SCD1-associated cancer). For example, methods and materials for using one or more stearoyl CoA desaturase 1 (SCD1) polypeptide inhibitors to treat a mammal having cancer (e.g., a SCD1-associated cancer) are provided.

14 Claims, 14 Drawing Sheets

(56) References Cited

OTHER PUBLICATIONS

Brown and Rudel, "Stearoyl-coenzyme A desaturase 1 inhibition and the metabolic syndrome: considerations for future drug discovery," Curr. Opin. Lipidol., 21(3):192-7, Jun. 2010.
Cao et al., "Sphereforming cell subpopulations with cancer stem cell properties in human hepatoma cell lines," BMC Gastroenterol., 11(1):71, Jun. 2011.
Cassidy et al., "Maintaining Tumor Heterogeneity in Patient-Derived Tumor Xenografts," Cancer Res., 75(15):2963-8, Aug. 2015.
Caulfield et al., "Motion of transfer RNA from the A/T state into the A-site using docking and simulations," Proteins., 80(11):2489-2500, Nov. 2012.
Chajès et al., "Association between Serum trans-Monounsaturated Fatty Acids and Breast Cancer Risk in the E3N-EPIC Study," Am. J. Epidemiol., 167(11):1312-20, Apr. 2008.
Chajès et al., "Riboli E. Fatty-acid composition in serum phospholipids and risk of breast cancer: An incident case-control study in Sweden," Intern. J. Cancer, 83(5):585-90, Nov. 1999.
Chang et al., "KGF induces lipogenic genes through a PI3K and JNK/SREBP-1 pathway in H292 cells," J. Lipid Res., 46(12):2624-35, Dec. 2005.
Chou and Talalay, "Quantitative analysis of dose-effect relationships: the combined effects of multiple drugs or enzyme inhibitors," Adv. Enzyme Regul., 22:27-55, 1984.
Chou et al., "Analysis of combined drug effects: a new look at a very old problem," Trends in Pharmacological Sciences., 4(11):450-454, 1983.
Chou et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., 86(20):1517-24, Oct. 1994.
Chou, "Drug Combination Studies and Their Synergy Quantification Using the Chou-Talalay Method," Cancer Res., 70(2):440-6, Jan. 2010.
Chow et al., "The Enhanced Metastatic Potential of Hepatocellular Carcinoma (HCC) Cells with Sorafenib Resistance," PLoS One, 8(11):e78675, Nov. 2013.
Conway et al., "Xenome—a tool for classifying reads from xenograft samples," Bioinformatics, 28(12):i172-8, Jun. 2012.
Cooper et al., "Current status of biomarker discovery in human clear cell renal cell carcinoma," J. Mol. Biomark Diagn., S2:1-10, 2012.
Copland et al., "Novel high-affinity PPARgamma agonist alone and in combination with paclitaxel inhibits human anaplastic thyroid carcinoma tumor growth via p21WAF1/CIP1," Oncogene., 25(16):2304-2317, Apr. 13, 2006.
Costello B. Navitoclax and Sorafenib Tosylate in Treating Patients with Relapsed or Refractory Solid Tumors.[http://www.cancer.gov/about-cancer/treatment/clinicaltrials/search/view?cdrid=761522&version=HealthProfessional&protocolsearchid=8215330 ]; 2014 [NCT02143401].
Currie et al., "Cellular Fatty Acid Metabolism and Cancer," Cell Metabolism, 18(2):153-61, Aug. 2013.
Database accession No. 1390035-79-6, [online] "1-Pi peraz i necarboxami de, 4-benzoyl-N-[2-[[(1,1 dimethylethyl)ami no] carbonyl]phenyl]-," Aug. 12, 2012, Abstract Only, 1 page.
Demoulin et al., "Platelet-derived Growth Factor Stimulates Membrane Lipid Synthesis Through Activation of Phosphatidylinositol 3-Kinase and Sterol Regulatory Element-binding Proteins," J. Biol. Chem., 279(34):35392-402, Aug. 2004.
Du et al., "FGFR3 Stimulates Stearoyl CoA Desaturase 1 Activity to Promote Bladder Tumor Growth," Cancer Res., 72(22):5843-55, Nov. 2012.
Du Manoir et al., "Breast tumor PDXs are genetically plastic and correspond to a subset of aggressive cancers prone to relapse," Mol. Oncol., 8(2):431-43, Mar. 2014.
Einarsdottir et al., "Melanoma patient-derived xenografts accurately model the disease and develop fast enough to guide treatment decisions," Oncotarget, 5(20):9609-18, Oct. 2014.

Extended European Search Report in International Application No. EP15830331.3, dated Mar. 9, 2018, 11 pages.
Falvella et al., "Stearoyl-CoA desaturase 1 (Scd1) gene overexpression is associated with genetic predisposition to hepatocarcinogenesis in mice and rats," Carcinogenesis, 23(11):1933-6, Nov. 2002.
Friesner et al., "Extra Precision Glide: Docking and Scoring Incorporating a Model of Hydrophobic Enclosure for Protein-Ligand Complexes," Journal of medicinal chemistry., 49(21):6177-6196, Oct. 19, 2006.
Fritz et al., "Abrogation of De novo Lipogenesis by Stearoyl-CoA Desaturase 1 Inhibition Interferes with Oncogenic Signaling and Blocks Prostate Cancer Progression in Mice," Mol. Cancer Therap., 9(6):1740-54, Jun. 2010.
Fu et al., "Discovery of new non-steroidal FXR ligands via a virtual screening workflow based on Phase shape and induced fit docking," Bioorg Med Chem Lett., 22(22):6848-6853, Nov. 15, 2012.
Gao et al., "High-throughput screening using patient-derived tumor xenografts to predict clinical trial drug response," Nat. Med., 21(11):1318-25, Oct. 2015.
GenBank® Accession No. AF097514.1 (GI No. 4808600), "*Homo sapiens* stearoyl-CoA desaturase (SCD) mRNA, complete cds," May 19, 1999, 2 pages.
GenBank® Accession No. O00767 (GI No. 21431730), "Acyl-CoA desaturase," Jul. 15, 1998, 11 pages.
Goodman et al., "Some practical improvements in the continual reassessment method for phase I studies," Stat. Med., 14(11):1149-61, Jun. 1995.
Gu et al., Autophagyrelated prognostic signature for breast cancer. Mol. Carcinogenesis, 55(3):292-9, Mar. 2016.
Guillou et al., "The key roles of elongases and desaturases in mammalian fatty acid metabolism: Insights from transgenic mice," Prog Lipid Res., 49(2):186-199, Apr. 2010.
Guo et al., "EGFR Signaling Through an Akt-SREBP-1-Dependent, Rapamycin-Resistant Pathway Sensitizes Glioblastomas to Antilipogenic Therapy," Sci. Signal., 2(101):ra82, Dec. 2009.
Halgren, "Identifying and characterizing binding sites and assessing druggability," J Chem Inf Model., 49(2):377-389, Feb. 2009.
Halgren, "New method for fast and accurate binding-site identification and analysis," Chem Biol Dru Des., 69(2):146-148, Feb. 2007.
Heitjan, "Biology, Models, and the Analysis of Tumor Xenograft Experiments," Clin. Cancer Res., 17(5):949-52, Jan. 2011.
Herr et al., "Drop-off during ribosome hopping," J Mol Biol., 311(3):445-452, Aug. 17, 2001.
Hess et al., "Inhibition of StearoylCoA Desaturase Activity Blocks Cell Cycle Progression and Induces Programmed Cell Death in Lung Cancer Cells," PLoS One, 5(6):e11394, Jun. 2010.
Hetz et al., "Targeting the unfolded protein response in disease," Nat Rev Drug Discov., 12(9):703-719, Sep. 2013.
Hidalgo et al., "Patient-Derived Xenograft Models: An Emerging Platform for Translational Cancer Research," Cancer Disc., 4(9):998-1013, Sep. 2014.
Hockla et al., "PRSS3/Mesotrypsin Is a Therapeutic Target for Metastatic Prostate Cancer," Mol. Cancer Res., 10(12):1555-66, Dec. 2012.
Holland et al., "Wnt signaling in stem and cancer stem cells," Curr. Opin. Cell Biol., 25(2):254-64., Apr. 2013.
Huang et al., "SCD1 negatively regulates autophagy-induced cell death in human hepatocellular carcinoma through inactivation of the AMPK signaling pathway," Cancer Lett.., 358(2):180-90, Mar. 2015.
Igal, "Stearoyl-CoA desaturase-1: a novel key player in the mechanisms of cell proliferation, programmed cell death and transformation to cancer," Carcinogenesis, 31(9):1509-15, Jul. 2010.
Izuishi et al., "Remarkable tolerance of tumor cells to nutrient deprivation: possible new biochemical target for cancer therapy," Cancer Res., 60(21):6201-7, Nov. 2000.
Jemal et al., "Global cancer statistics," CA Cancer J. Clin., 61(2):69-90, Feb. 2011.
Jorgensen et al., "The OPLS [optimized potentials for liquid simulations] potential functions for proteins, energy minimizations for crystals of cyclic peptides and crambin," J Am Chem Soc., 110(6):1657-1666, Mar. 1, 1988.

(56) References Cited

OTHER PUBLICATIONS

Kalari et al., "MAP-RSeq: Mayo Analysis Pipeline for RNA sequencing," BMC Bioinformatics, 15(1):1-11, Jun. 2014.
Kalid et al., "Consensus Induced Fit Docking (cIFD): methodology, validation, and application to the discovery of novel Crm1 inhibitors," J Comput Aided Mol Des., 26(11):1217-1228, Nov. 2012.
Kim et al., "Cell death and endoplasmic reticulum stress: disease relevance and therapeutic opportunities," Nat Rev Drug Discov., 7(12):1013-1030, Dec. 2008.
Kim et al., "Stearoyl CoA desaturase (SCD) facilitates proliferation of prostate cancer cells through enhancement of androgen receptor transactivation," Mol. Cells, 31(4):371-7, Apr. 2011.
Koltun et al., "Novel, potent, selective, and metabolically stable stearoyl-CoA desaturase (SCD) inhibitors," Bioorganic Medicinal Chem Lett., 19(7):2048-2052, Apr. 1, 2009.
Krieger et al., "Assignment of protonation states in proteins and ligands: combining pKa prediction with hydrogen bonding network optimization.," Methods Mol Biol., 819:405-421, 2012.
Krieger et al., "Improving physical realism, stereochemistry, and side-chain accuracy in homology modeling: Four approaches that performed well in CASP8," Proteins., 77(Suppl S9):114-122, 2009.
Kuhajda et al., "Fatty acid synthesis: a potential selective target for antineoplastic therapy," Proc. Natl. Acad. Sci. USA, 91(14):6379-83, 1994.
Kupershmidt et al., Ontology-based meta-analysis of global collections of high-throughput public data, PLoS One., 5(9):e13066, 13 pages Sep. 2010.
Lee et al., "Nutrient-sensing nuclear receptors coordinate autophagy," Nature, 516(7529):112-5, Nov. 2014.
Lee et al., "Patient-Derived Xenografts from Non-Small Cell Lung Cancer Brain Metastases Are Valuable Translational Platforms for the Development of Personalized Targeted Therapy," Clin. Cancer Res., 21(5):1172-82, Mar. 2015.
Leger et al., "Synthesis and biological activity of a potent and orally bioavailable SCD inhibitor (MF-438)," Bioorg Med Chem Lett., 20(2):499-502, Jan. 15, 2010.
Leung and Kim, "Stearoyl Co-A Desaturase 1 as a ccRCC Therapeutic Target: Death by Stress," Clin. Cancer Res., 19(12):1-3, May 2013.
Li et al., "Endocrine-Therapy-Resistant ESR1 Variants Revealed by Genomic Characterization of Breast-Cancer-Derived Xenografts," Cell Reports, 4(6):1116-30, Sep. 2013.
Li et al., "SCD1 expression is dispensable for hepatocarcinogenesis induced by AKT and ras oncogenes in mice," Plos one., 8(9):e75104, Sep. 19, 2013, 12 pages.
Li et al., "Targeted hepatocellular carcinoma proapoptotic BikDD gene therapy," Oncogene, 30(15):1773-83, 2011.
Li et al., "Thiazole analog as stearoyl-CoA desaturase 1 inhibitor," Bioorg Med Chem Lett., 19(17):5214-5217, Epub Jul. 9, 2009.
Liang and Sha, "Modeling antitumor activity by using a non-linear mixed-effects model," Math. Biosci., 189(1):61-73, May 2004.
Liu et al., "Discovery of potent, selective, orally bioavailable stearoyl-CoA desaturase 1 inhibitors," J Med Chem., 50(13):3086-3100, Jun. 28, 2007.
Liu, "Stearoyl-CoA desaturase inhibitors: update on patented compounds," Expert Opin Ther Pat., 19(9):1169-1191, 2009.
Llovet et al., "Sorafenib in Advanced Hepatocellular Carcinoma," N. Engl. J. Med., 359(4):378-90, Jul. 2008.
Loving et al., "Energetic analysis of fragment docking and application to structure-based pharmacophore hypothesis generation," J computer-aided molecular design., 23(8):541-554, Aug. 2009.
Luyimbazi et al., "Rapamycin regulates stearoyl CoA desaturase 1 expression in breast cancer," Mol. Cancer Ther., 9(10):2770-84, Oct. 2010.
Marlow et al., "Detailed molecular fingerprinting of four new anaplastic thyroid carcinoma cell lines and their use for verification of RhoB as a molecular therapeutic target," J Clin Endocrinol Metab., 95(12):5338-5347, 2010.

Marlow et al., "FoxO3a drives proliferation in anaplastic thyroid carcinoma through transcriptional regulation of cyclin A1: a paradigm shift that impacts current therapeutic strategies," J. Cell Sci., 125(18):4253-63, Sep. 2012.
Mason et al., "SCD1 Inhibition Causes Cancer Cell Death by Depleting Mono-Unsaturated Fatty Acids," PLoS One, 7(3):e33823, Mar. 2012.
Mauvoisin et al., "Decreasing stearoyl-CoA desaturase-1 expression inhibits β-catenin signaling in breast cancer cells," Cancer Sci., 104(1):36-42, Jan. 2013.
MedicineNet.com (http://www.medterms.com, 2004).
Menendez and Lupu, "Fatty acid synthase and the lipogenic phenotype in cancer pathogenesis," Nat. Rev. Cancer, 7(10):763-77, Oct. 2007.
Minville-Walz et al., "Inhibition of Stearoyl-CoA Desaturase 1 Expression Induces CHOP-Dependent Cell Death in Human Cancer Cells," PLoS One, 5(12):e14363, Dec. 2010.
Mohamadi et al., "Macromodel—an integrated software system for modeling organic and bioorganic molecules using molecular mechanics," J Comput Chem., 11(4):440-467, May 1990.
Monsma et al., "Using a rhabdomyosarcoma patient-derived xenograft to examine precision medicine approaches and model acquired resistance," Pediatr. Blood Cance, 61(9):1570-7, Mar. 2014.
Mounier et al., "Lipogenesis in cancer progression (review)," Int. J. Oncol., 45:485-92, May 2014.
Muir et al., "Proteomic and Lipidomic Signatures of Lipid Metabolism in NASH-Associated Hepatocellular Carcinoma," Cancer Res., 73(15):4722-31, Aug. 2013.
Naugler et al., "Gender Disparity in Liver Cancer Due to Sex Differences in MyD88-Dependent IL-6 Production," Science, 317(5834):121-4, Jul. 2007.
Nelson et al., "Transcriptional changes associated with reduced spontaneous liver tumor incidence in mice chronically exposed to high dose arsenic," Toxicol., 266(1-3):6-15, Dec. 2009.
Nile and Hannoush, "Fatty acylation of Wnt proteins," Nat. Chem. Biol., 12(2):60-9, Jan. 2016.
Niso-Santano et al., "Unsaturated fatty acids induce non-canonical autophagy," EMBO J., 34(8):1025-41, Jan. 2015.
Noto et al., "Stearoyl-CoA desaturase-1 is a key factor for lung cancer-initiating cells," Cell Death Dis., 4(12):e947, Dec. 2013.
Oballa et al., "Development of a liver-targeted stearoyl-CoA desaturase (SCD) inhibitor (MK-8245) to establish a therapeutic window for the treatment of diabetes and dyslipidemia," J Med Chem., 54(14):5082-5096, Epub Jun. 28, 2011.
Oesterreich et al., "Using Mice to Treat (Wo)men: Mining Genetic Changes in Patient Xenografts to Attack Breast Cancer," Cell Reports, 4(6):1061-2, Sep. 2013.
Okuda, "Epidemiology of primary liver cancer," Primary Liver Cancer in Japan, Tobe T (ed)., Chapter 1, pp. 3-15, 1992.
O'Quigley et al., "Continual reassessment method: a practical design for phase 1 clinical trials in cancer," Biometrics, 46(1):33-48, Mar. 1990.
Pala et al., "Erythrocyte Membrane Fatty Acids and Subsequent Breast Cancer: a Prospective Italian Study," J. Natl. Cancer Institute, 93(14):1088-95, Jul. 2001.
Pala et al., "Structure-Based Virtual Screening of MT2 Melatonin Receptor: Influence of Template Choice and Structural Refinement," J Chem Inf Model., 53(4):821-835, Mar. 29, 2013.
Patani and LaVoie, "Bioisosterism: A Rational Approach in Drug Design," Chem. Rev., 96(8):3147-3176, 1996.
Paton and Ntambi, "Biochemical and physiological function of stearoyl-CoA desaturase," Am. J. Physiol. Endocrinol. Metab., 297(1):E28-37, Jul. 2009.
Petrek et al., "Fatty acid composition of adipose tissue, an indication of dietary fatty acids, and breast cancer prognosis," J. Clin. Oncol., 15(4):1377-84, Apr. 1997.
Porstmann et al., "PKB//Akt induces transcription of enzymes involved in cholesterol and fatty acid biosynthesis via activation of SREBP," Oncogene, 24(43):6465-81, Jun. 2005.
Porstmann et al., "SREBP Activity Is Regulated by mTORC1 and Contributes to Akt-Dependent Cell Growth," Cell Metab., 8(3):224-36, Sep. 2008.

(56) References Cited

OTHER PUBLICATIONS

Powell et al., "2-Aryl benzimidazoles: human SCD1-specific stearoyl coenzyme-A desaturase inhibitors," Bioorg Med Chem Lett., 20(22):6366-6369, Nov. 15, 2010.

Powers, "Cell Growth Control: mTOR Takes on Fat," Mol. Cell, 31(6):775-6, Sep. 2008.

Pubchem, Substance Record for SID 144964572, AKOS008653309, Available Oct. 18, 2012, retrieved on Oct. 30, 2015, Retrieved from the Internet, URL: https://pubchem.ncbi.nlm.nih.gov/substance/144964572/version/1>, 6 pages.

Rathert et al., "Transcriptional plasticity promotes primary and acquired resistance to BET inhibition," Nature, 525(7570):543-7, Sep. 2015.

Reya and Clevers, "Wnt signalling in stem cells and cancer," Nature, 434(7035):843-50, Apr. 2005.

Roemeling et al., "Stearoyl-CoA Desaturase 1 Is a Novel Molecular Therapeutic Target for Clear Cell Renal Cell Carcinoma," Clin Canc Res., 19(9):2368-2380, Apr. 30, 2013.

Roongta et al., "Cancer cell dependence on unsaturated fatty acids implicates stearoyl-CoA desaturase as a target for cancer therapy," Mol Cancer Res., 9(11):1551-1561, Nov. 2011.

Roongta et al., "Cancer Cell Dependence on Unsaturated Fatty Acids Implicates Stearoyl-CoA Desaturase as a Target for Cancer Therapy," Mol. Cancer Res., 9(11):1551-61, Nov. 2011.

Ruddigkeit et al., "Visualization and virtual screening of the chemical universe database GDB-17," J Chem Inf Model., 53(1):56-65, Dec. 23, 2012.

Sampath and Ntambi, "The role of stearoyl-CoA desaturase in obesity, insulin resistance, and inflammation," Ann. N.Y Acad. Sci., 1243(1):47-53, Dec. 2011.

Sandor et al., "Virtual Fragment Docking by Glide: a Validation Study on 190 Protein-Fragment Complexes," J Chem Inf Model., 50(6):1165-1172, Jun. 2010.

Sastry et al., "Boosting Virtual Screening Enrichments with Data Fusion: Coalescing Hits from Two-Dimensional Fingerprints, Shape, and Docking," J Chem Inf Model., 53(7):1531-1542, 2013.

Sastry et al., "Rapid Shape-Based Ligand Alignment and Virtual Screening Method Based on Atom/Feature-Pair Similarities and Volume Overlap Scoring ," J Chem Inf Model., 51(10):2455-2466, Sep. 15, 2011.

Scaglia et al., "Inhibition of StearoylCoA Desaturase-1 Inactivates Acetyl-CoA Carboxylase and Impairs Proliferation in Cancer Cells: Role of AMPK," PLoS One, 4(8):e6812, Aug. 2009.

Schlaepfer et al., "Progestin modulates the lipid profile and sensitivity of breast cancer cells to docetaxel," Mol. Cell. Endocrin., 363(1-2):111-21, Aug. 2012.

Schmittgen et al., "Analyzing real-time PCR data by the comparative C(T) method," Nat Protoc., 3(6): 1101-1108, 2008.

Seok et al., "Transcriptional regulation of autophagy by an FXR-CREB axis," Nature, 516(7529):108-11, Dec. 2014.

Siolas and Hannon, "Patient-Derived Tumor Xenografts: Transforming Clinical Samples into Mouse Models," Cancer Res., 73(17):5315-9, Sep. 2013.

Song et al., "Hypoxia-induced autophagy contributes to the chemoresistance of hepatocellular carcinoma cells," Autophagy, 5(8):1131-44, Nov. 2009.

Sorafenib Package Insert and Prescribing Information. 2010.

Sperandio et al., "MED-SuMoLig: A New Ligand-Based Screening Tool for Efficient Scaffold Hopping," J Chem Inf Model., 47(3):1097-1110, 2007.

Sun, "Classification of scaffold-hopping approaches," Drug discovery today., 17(7-8):310-324, Apr. 2012.

Tun et al., "Pathway signature of clear cell renal cell carcinoma," PLoS One, 5:e10696, May 2010.

Tusher et al., "Significance analysis of microarrays applied to the ionizing radiation response," Proc. Natl. Acad. Sci. USA, 98(9):5116-21, Apr. 2001.

Uto et al., "Discovery of novel SCD1 inhibitors: 5-Alkyl-4,5-dihydro-3H-spiro[1,5-benzoxazepine-2,4'-piperidine] analogs," Eur J Med Chem., 46(5):1892-1896, May 2011.

Uto et al., "Synthesis and evaluation of novel stearoyl-CoA desaturase 1 inhibitors: 1'-{6-[5-(pyridin-3-ylmethyl)-1,3,4-oxadiazol-2-yl]pyridazin-3-yl}-3,4-dihydrospiro[chromene-2,4'-piperidine] analogs," Eur J Med Chem., 45(11):4788-4796, Nov. 2010.

Vivoli et al., "Inhibition of Prohormone Convertases PC1/3 and PC2 by 2,5-Dideoxystreptamine Derivatives," Mol Pharmacol., 81(3):440-454, Mar. 2012.

Von Roemeling and Copland, "Targeting lipid metabolism for the treatment of anaplastic thyroid carcinoma," Expert Opin. Ther. Targets, 20(2):159-66, Sep. 2015.

Von Roemeling et al., "Aberrant Lipid Metabolism in Anaplastic Thyroid Carcinoma Reveals Stearoyl CoA Desaturase 1 as a Novel Therapeutic Target," J. Clin. Endocrinol. Metab., 100(5):E697-709, May 2015.

Von Roemeling et al., "Functional genomics identifies novel genes essential for clear cell renal cell carcinoma tumor cell proliferation and migration," Oncotarget, 5(14):5320-34, Jun. 2014.

Von Roemeling et al., "Neuronal Pentraxin 2 is a regulator of clear cell renal cell carcinoma malignancy through activation of the AMPA-selective glutamate receptor-4," Cancer Res., 75(17):4796-810, Jun. 2014.

Von Roemeling et al., "Stearoyl-CoA Desaturase 1 Is a Novel Molecular Therapeutic Target for Clear Cell Renal Cell Carcinoma," Clin. Cancer Res., 19(9):2368-80, May 2013.

Voss et al., "Discovery and pharmacological characterization of SAR707 as novel and selective small molecule inhibitor of stearoyl-CoA desaturase (SCD1)," Eur. J. Pharmacol., 707(1-3):140-6, May 2013.

Walter., "The unfolded protein response: from stress pathway to homeostatic regulation," Science., 334(6059):1081-1086, Nov. 25, 2011.

Wang and Shen et al., "Activation of ATF6 and an ATF6 DNA binding site by the endoplasmic reticulum stress response," J Biol Chem., 275(35):27013-27020, Sep. 1, 2000.

Watts et al., "A Conformational Search Method for Efficient Generation of Bioactive Conformers," J Chem Inf Model., 50(4):534-546, Apr. 26, 2010.

Whittle et al., "Patient-derived xenograft models of breast cancer and their predictive power," Breast Cancer Res., 17(1):17, Feb. 2015.

Wu and Irizarry, "Preprocessing of oligonucleotide array data," Nat. Biotechnol., 22(6):656-8, Jun. 2004.

Xin et al., "Discovery of piperidine-aryl urea-based stearoyl-CoA desaturase 1 inhibitors," Bioorg Med Chem Lett., 18(15):4298-4302, Aug. 1, 2008.

Xu et al., "Endoplasmic reticulum stress: cell life and death decisions," J Clin Invest., 115(10):2656-2664, Oct. 2005.

Zhang et al., "Positive feedback loop and synergistic effects on promoting tumorgenesis between HIF-2α and SCD1 in clear cell renal cell carcinoma," Cancer Sci., 104:416-22, Apr. 2013.

Zhang et al., "Proteomic Study Reveals That Proteins Involved in Metabolic and Detoxification Pathways Are Highly Expressed in HER-2/neu-positive Breast Cancer," Mol. Cell. Proteomics, 4(11):1686-96, Nov. 2005.

Zhang et al., "Screening of kinase inhibitors targeting BRAF for regulating autophagy based on kinase pathways," Mol. Med. Rep., 9(1):83-90, Jan. 2014.

Zhao et al., "Bayesian Hierarchical Changepoint Methods in Modeling the Tumor Growth Profiles in Xenograft Experiments," Clin. Cancer Res., 17(5):1057-64, Mar. 2011.

Zhou., "Improving threading algorithms for remote homology modeling by combining fragment and template comparisons," Proteins., 78(9):2041-2048, Jul. 2010.

Zhou., "Protein structure prediction by Pro-Sp3-TASSER," Biophys J., 96(6):2119-2127, Mar. 2009.

Zhou., "Template-based protein structure modeling using TASSER(VMT)," Proteins., 80(22);352-361, Feb. 2012.

Zureik et al., "Fatty acid proportions in cholesterol esters and risk of premature death from cancer in middle aged French men," BMJ. 311(7015):1251-4, Aug. 1995.

U.S. Appl. No. 15/502,301, filed Feb. 7, 2017, John A. Copland III, Issued.

(56) References Cited

OTHER PUBLICATIONS

U.S. Appl. No. 16/422,519, filed May 24, 2019, John A. Copland III, Published.
U.S. Appl. No. 16/489,133, filed Aug. 27, 2019, Christina Von Roemeling, Pending.
Abramson, "The lipogenesis pathway as a cancer target," J. Med. Chem., 54(16):5615-38, Aug. 2011.
Baenke et al., "Hooked on fat: the role of lipid synthesis in cancer metabolism and tumour development," Dis. Model Mech., 6(6):1353-63, Nov. 2013.
Beloribi-Djefaflia et al., "Lipid metabolic reprogramming in cancer cells," Oncogenesis, 5(1):e189, Jan. 2016.
Dholaria et al., "Emerging therapeutic agents for lung cancer," Journal of hematology & oncology, 9(1):138, Dec. 2016.
Fucikova et al., "Prognostic and predictive value of DAMPs and DAMP-associated processes in cancer," Front Immunol., 6:402, Aug. 2015.
Goldberg and Drake, "LAG-3 in Cancer Immunotherapy," Curr. Top Microbiol. Immunol., 344:269-78, Nov. 2010.
Guo et al., "Therapeutic cancer vaccines: past, present, and future," Adv. Cancer Res., 119:421-75, Jan. 2013.
Hanahan and Weinberg, "Hallmarks of cancer: the next generation," Cell, 144(5):646-74, Mar. 2011.
Huard et al., "Cellular expression and tissue distribution of the human LAG-3-encoded protein, an MHC class II ligand," Immunogenetics, 39(3):213-217, Jan. 1994.
Ide et al., "Human breast cancer tissues contain abundant phosphatidylcholine (36:1) with high stearoyl-CoA desaturase-1 expression," PLoS One, 8(4):e61204, 2013.
Janssens et al., "Emerging functions of the unfolded protein response in immunity," Nat. Immunol., 15(10):910-9, Oct. 2014.
Mellman et al., "Cancer immunotherapy comes of age," Nature, 480(7378):480-9, Dec. 2011.
Panaretakis et al., "Mechanisms of pre-apoptotic calreticulin exposure in immunogenic cell death," EMBO J., 28(5):578-90, Mar. 2009.
Petrova et al., "TTI-621 (SIRPαFc): a CD47-blocking innate immune checkpoint inhibitor with broad antitumor activity and minimal erythrocyte binding," Clinical Cancer Research, 23(4):1068-79, Feb. 2017.
Rodvold et al., "Immune modulation by ER stress and inflammation in the tumor microenvironment," Cancer Letters, 380(1):227-36, Sep. 2016.
Roemeling et al., "Aberrant lipid metabolism in anaplastic thyroid carcinoma reveals stearoyl CoA desaturase 1 as a novel therapeutic target," J. Clin. Endocrinol. Metab., 100(5): E697-E709, May 2015.
Rosenberg, "Raising the bar: the curative potential of human cancer immunotherapy," Sci. Transl. Med., 4(127):127ps8, Mar. 2012.
Rysman et al., "De novo lipogenesis protects cancer cells from free radicals and chemotherapeutics by promoting membrane lipid saturation," Cancer Res., 70(20):8117-26, Oct. 2010.
Santos and Schulze, "Lipid metabolism in cancer," FEBS J., 279(15):2610-23, Aug. 2012.
Woo et al., "Innate immune recognition of cancer," Annual review of immunology, 33:445-74, Mar. 2015.
Yahagi et al., "Co-ordinate activation of lipogenic enzymes in hepatocellular carcinoma," European Journal of Cancer, 41(9):1316-22, Jun. 2005.
Zhang and Du, "Dysregulated lipid metabolism in cancer," World journal of biological chemistry, 3(8):167, Aug. 2012.
Wurz et al., "Novel cancer antigens for personalized immunotherapies: latest evidence and clinical potential," Ther. Adv. Med. Oncology, 8(1):4-31, Jan. 2016.

* cited by examiner

| Dose (mg/kg) | 10 | 30 | 100 |
|---|---|---|---|
| Cmax (ng/mL) | 4323 | 15900 | 43267 |
| AUC (ng*h/mL) | 20922 | 71229 | 336456 |
| Cmax/D | 432 | 530 | 433 |
| AUC/D | 2092 | 2374 | 3365 |
| T1/2 (h) | 3.48 | 2.71 | 3.94 |
| Bioavailability (%)[a] | 119 | 152 | 212 |

ASSESSING AND TREATING CANCER

CROSS-REFERENCE TO RELATED APPLICATIONS

This application claims the benefit of U.S. Provisional Application Ser. No. 62/650,217, filed Mar. 29, 2018. The disclosure of the prior application is considered part of (and is incorporated by reference in) the disclosure of this application.

BACKGROUND

1. Technical Field

This document relates to methods and materials for identifying and/or treating mammals having cancer (e.g., a SCD1-associated cancer). For example, this document provides methods and materials for using one or more stearoyl CoA desaturase 1 (SCD1) polypeptide inhibitors to treat a mammal having cancer (e.g., a SCD1-associated cancer).

2. Background Information

Hepatocellular carcinoma (HCC) is the sixth most prevalent malignancy worldwide and is a rising cause of cancer related mortality. The American Cancer Society predicts that about 40,710 new cases of HCC will be diagnosed in 2017, with about 28,920 people (19,610 men and 9,310 women) expected to die of these cancers (American Cancer Society's Cancer Statistics Center).

SUMMARY

This document provides methods and materials for identifying and/or treating mammals (e.g., humans) having cancer (e.g., a SCD1-associated cancer). For example, this document provides methods and materials for detecting the presence of an elevated level of SCD1 polypeptides within a mammal and identifying the mammal as having a SCD1-associated cancer. As demonstrated herein, SCD1 polypeptides are present in liver cells (e.g., liver cancer cells) of humans, and Wnt regulated polypeptides, survivin and cMyc, were elevated in selective SCD1 inhibitor (SSI) responsive liver cells. In some cases, this document provides methods and materials for assessing a mammal having cancer (e.g., a SCD1-associated cancer). For example, the presence of an elevated level of one or more Wnt regulated polypeptides (e.g., cMyc and/or survivin) can be used to identify a mammal as having a SCD1-associated cancer that is responsive to one or more SCD1 polypeptide inhibitors. In some cases, this document provides methods and materials for treating a mammal having cancer (e.g., a SCD1-associated cancer) and/or identified as having a SCD1-associated cancer that is responsive to one or more SCD1 polypeptide inhibitors by administering one or more SCD1 polypeptide inhibitors. For example, a mammal having a SCD1-associated cancer (e.g., a SCD1-associated cancer that is responsive to one or more SCD1 polypeptide inhibitors) can be administered one or more SCD1 polypeptide inhibitors to treat the mammal.

In general, one aspect of this document features methods for treating a cancer in a mammal identified as having a cancer exhibiting SCD1 polypeptide expression. The methods can include, or consist essentially of, detecting an elevated level of cMyc polypeptides within the biological sample from said mammal, and administering a SCD1 polypeptide inhibitor to the mammal. The mammal can be a human. The cancer can be liver cancer, renal cell carcinoma, ovarian cancer, breast cancer, prostate cancer, colon cancer, pancreatic cancer, bladder cancer, lung cancer, thyroid cancer, brain cancer, melanoma, or lymphoma. In some cases, the cancer can be liver cancer (e.g., a hepatocellular carcinoma or a cholangiocarcinoma). The method also can include detecting an elevated level of survivin polypeptides within the biological sample from the mammal. The SCD1 polypeptide inhibitor can be a compound having Formula (II) or Formula (IIa):

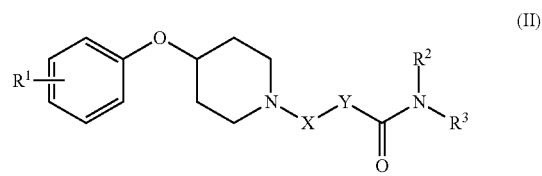

(II)

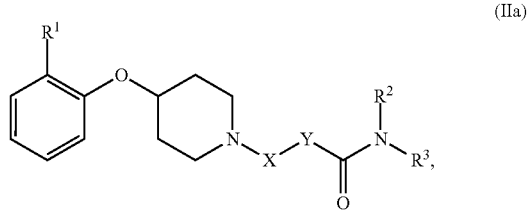

(IIa)

or pharmaceutically acceptable salt thereof, where $R^1$ is halo, X is $-(C=O)NR^4-$, Y is

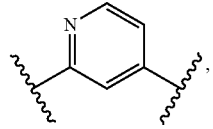 [SMILES: *c1ccnc(*)c1]

and $R^2$, $R^3$, and $R^4$ are each independently H or an unsubstituted $C_{1-6}$alkyl. In some cases, the SCD1 polypeptide inhibitor can be SSI-4, 2-{[4-(2-Chlorophenoxy)piperidine-1-carbonyl]amino}-N-methylpyridine-4-carboxamide:

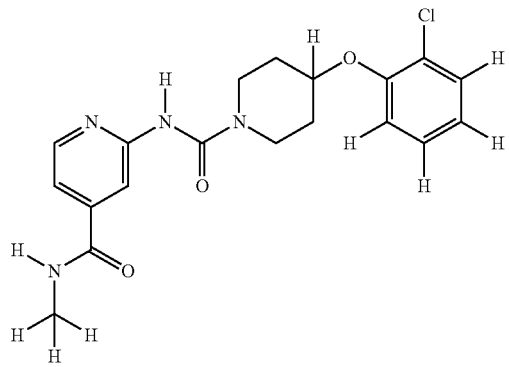 [SMILES: CNC(=O)c1ccnc(NC(=O)N2CCC(Oc3ccccc3Cl)CC2)c1]

or pharmaceutically acceptable salt thereof. The SCD1 polypeptide inhibitor can be a compound having Formula (I) or Formula (Ia):

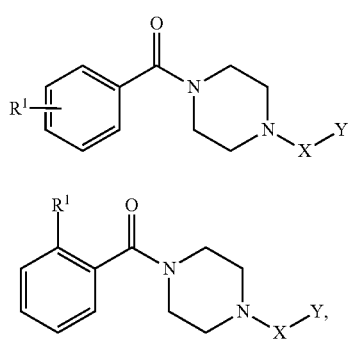

(I)

(Ia)

or a pharmaceutically acceptable salt thereof, where $R^1$ is an unsubstituted $C_{1-6}$alkyl or $C_{1-6}$haloalkyl; X is

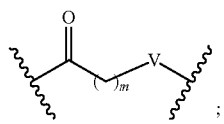

Y is selected from:

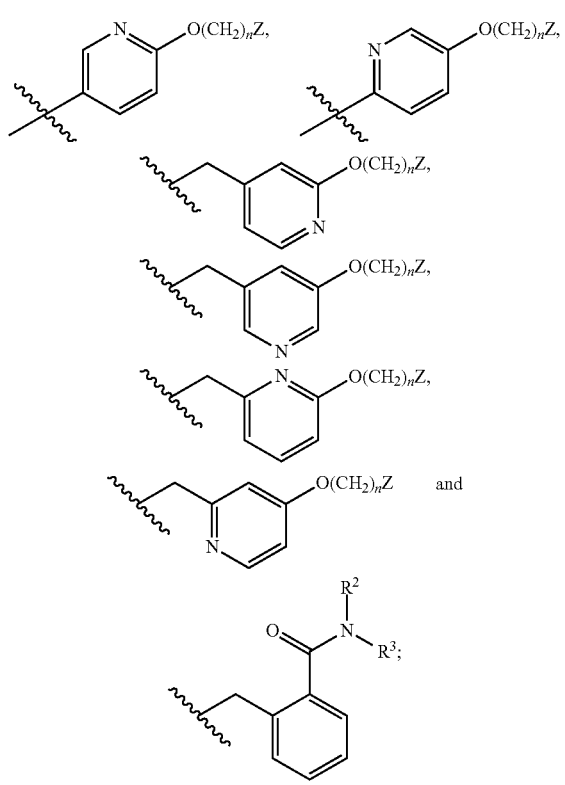

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, the SCD1 polypeptide inhibitor can be SSI-2, 2-(benzyloxy)-5-{[hydroxy({4-[2-(trifluoromethyl)benzoyl]piperazin-1-yl})methyl]amino}-1,2-dihydropyridin-2-ylium-1-ide:

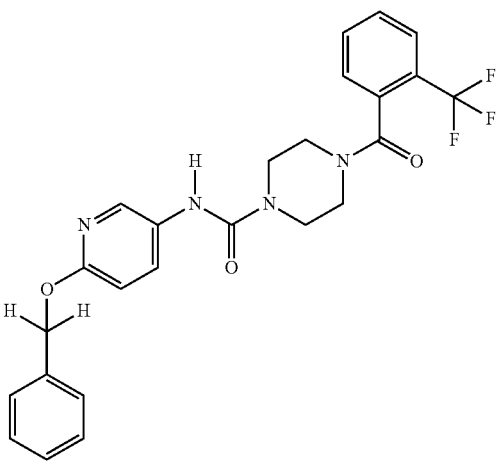 [SMILES: O=C(Nc1ccc(OCc2ccccc2)nc1)N1CCN(C(=O)c2ccccc2C(F)(F)F)CC1]

or pharmaceutically acceptable salt thereof. The method also can include administering an additional therapeutic agent used to treat cancer to the mammal. The additional therapeutic agent can be a chemotherapeutic agent. The chemotherapeutic agent can be a kinase inhibitor. The kinase inhibitor can be sorafenib, regorafenib, bortezomib, erlotinib, gefitinib, imatinib, vemurafenib, or vismodegib. For example, the kinase inhibitor can be sorafenib.

In another aspect, this document features methods for treating a cancer in a mammal identified as having a cancer exhibiting SCD1 polypeptide expression and an elevated level of cMyc polypeptides. The methods can include, or consist essentially of, administering a SCD1 polypeptide inhibitor to the mammal. The mammal can be a human. The cancer can be liver cancer, renal cell carcinoma, ovarian cancer, breast cancer, prostate cancer, colon cancer, pancreatic cancer, bladder cancer, lung cancer, thyroid cancer, brain cancer, melanoma, or lymphoma. In some cases, the cancer can be liver cancer (e.g., a hepatocellular carcinoma or a cholangiocarcinoma). The method also can include detecting an elevated level of survivin polypeptides within the biological sample from the mammal. The SCD1 polypeptide inhibitor can be a compound having Formula (II) or Formula (IIa):

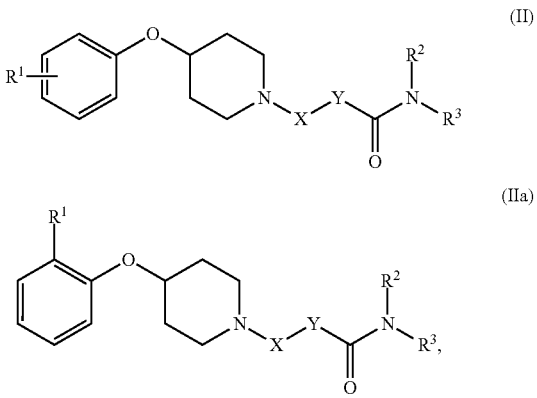

or pharmaceutically acceptable salt thereof, where $R^1$ is halo, X is $—(C=O)NR^4—$, Y is

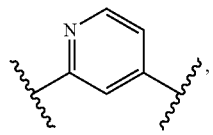 [SMILES: *c1ccnc(*)c1]

and $R^2$, $R^3$, and $R^4$ are each independently H or an unsubstituted $C_{1-6}$alkyl. In some cases, the SCD1 polypeptide inhibitor can be SSI-4, 2-{[4-(2-Chlorophenoxy)piperidine-1-carbonyl]amino}-N-methylpyridine-4-carboxamide:

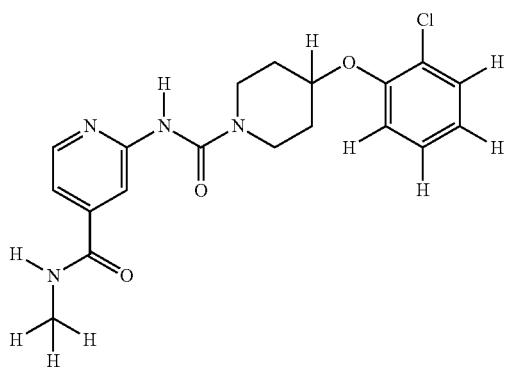 [SMILES: CNC(=O)c1ccnc(NC(=O)N2CCC(Oc3ccccc3Cl)CC2)c1]

or pharmaceutically acceptable salt thereof. The SCD1 polypeptide inhibitor can be a compound having Formula (I) or Formula (Ia):

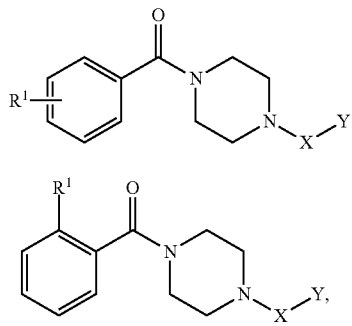

or a pharmaceutically acceptable salt thereof, where $R^1$ is an unsubstituted $C_{1-6}$alkyl or $C_{1-6}$haloalkyl; X is

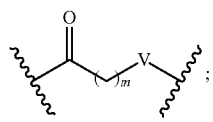

Y is selected from:

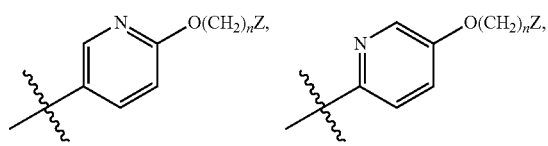

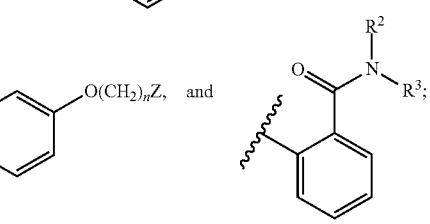

$m$ is 0 or 1; $n$ is 0, 1, or 2; V is $NR^4$ or O; $R^2$, $R^3$, and $R^4$ are each independently H or an unsubstituted $C_{1-6}$alkyl; and Z is an unsubstituted aryl. In some cases, the SCD1 polypeptide inhibitor can be SSI-2, 2-(benzyloxy)-5-{[hydroxy({4-[2-(trifluoromethyl)benzoyl]piperazin-1-yl})methyl]amino}-1,2-dihydropyridin-2-ylium-1-ide:

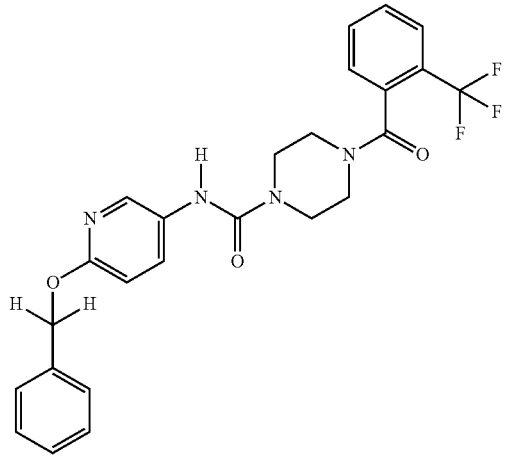 [SMILES: O=C(Nc1ccc(OCc2ccccc2)nc1)N1CCN(C(=O)c2ccccc2C(F)(F)F)CC1]

or pharmaceutically acceptable salt thereof. The method also can include administering an additional therapeutic agent used to treat cancer to the mammal. The additional therapeutic agent can be a chemotherapeutic agent. The chemotherapeutic agent can be a kinase inhibitor. The kinase inhibitor can be sorafenib, regorafenib, bortezomib, erlotinib, gefitinib, imatinib, vemurafenib, or vismodegib. For example, the kinase inhibitor can be sorafenib.

In another aspect, this document features methods for treating a cancer in a mammal. The methods can include, or consist essentially of, detecting SCD1 polypeptide expression within a biological sample from the mammal, detecting an elevated level of cMyc polypeptides within the biological sample from the mammal, and administering a SCD1 polypeptide inhibitor to the mammal. The mammal can be a human. The cancer can be liver cancer, renal cell carcinoma, ovarian cancer, breast cancer, prostate cancer, colon cancer, pancreatic cancer, bladder cancer, lung cancer, thyroid cancer, brain cancer, melanoma, or lymphoma. In some cases, the cancer can be liver cancer (e.g., a hepatocellular carcinoma or a cholangiocarcinoma). The method also can include detecting an elevated level of survivin polypeptides within the biological sample from the mammal. The SCD1 polypeptide inhibitor can be a compound having Formula (II) or Formula (IIa):

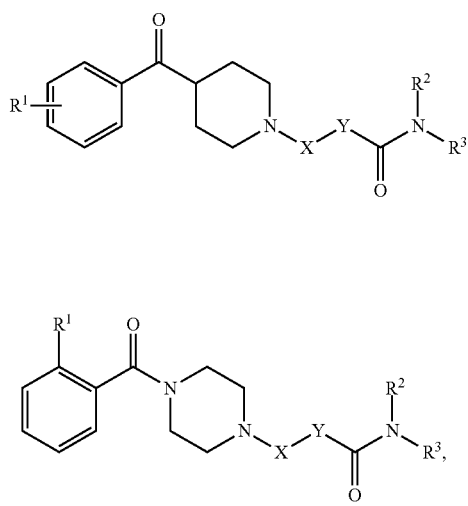

(II)

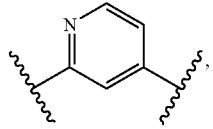 [SMILES: *c1ccnc(*)c1]

(IIa)

or pharmaceutically salt thereof, where $R^1$ is halo, X is —(C═O)$NR^4$—, Y is and $R^2$, $R^3$, and $R^4$ are each independently H or an unsubstituted $C_{1-6}$alkyl. In some cases, the SCD1 polypeptide inhibitor can be SSI-4, 2-{[4-(2-Chlorophenoxy)piperidine-1-carbonyl]amino}-N-methylpyridine-4-carboxamide:

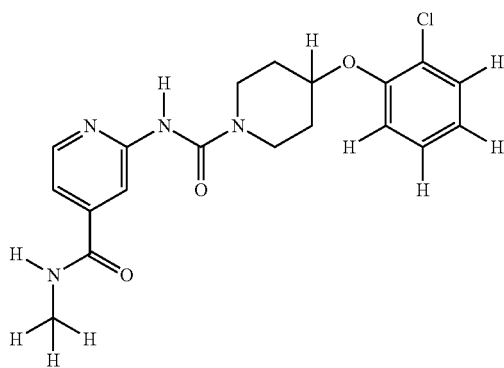 [SMILES: CNC(=O)c1ccnc(NC(=O)N2CCC(Oc3ccccc3Cl)CC2)c1]

or pharmaceutically acceptable salt thereof. The SCD1 polypeptide inhibitor can be a compound having Formula (I) or Formula (Ia):

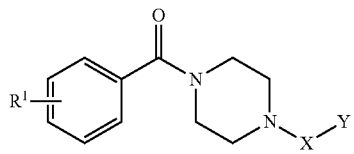

(I)

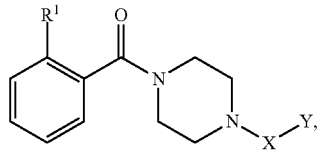

(Ia)

or a pharmaceutically acceptable salt thereof, where $R^1$ is an unsubstituted $C_{1-6}$alkyl or $C_{1-6}$haloalkyl; X is

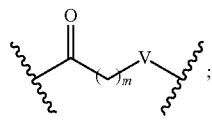

Y is selected from:

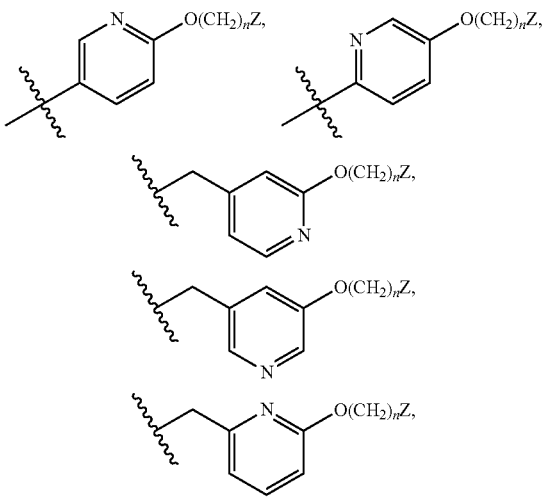

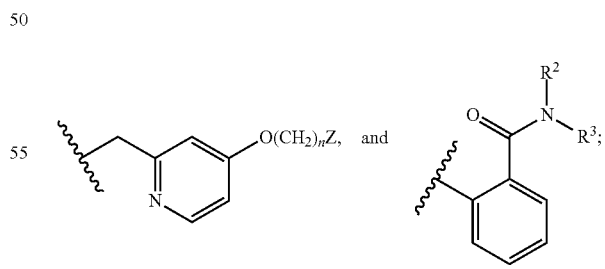

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, the SCD1 polypeptide inhibitor can be SSI-2, 2-(benzyloxy)-5-{[hydroxy({4-[2-(trifluoromethyl)benzoyl]piperazin-1-yl})methyl]amino}-1,2-dihydropyridin-2-ylium-1-ide:

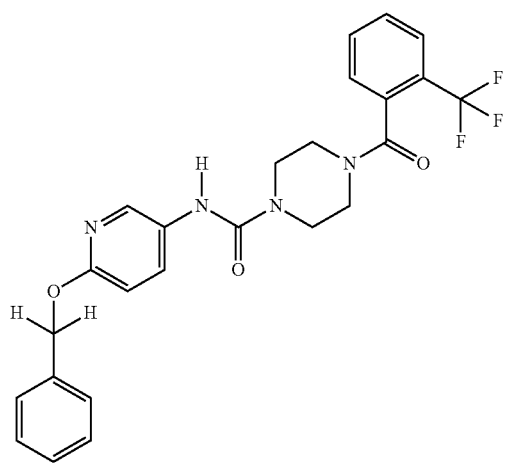 [SMILES: O=C(Nc1ccc(OCc2ccccc2)nc1)N1CCN(C(=O)c2ccccc2C(F)(F)F)CC1]

or pharmaceutically acceptable salt thereof. The method also can include administering an additional therapeutic agent used to treat cancer to the mammal. The additional therapeutic agent can be a chemotherapeutic agent. The chemotherapeutic agent can be a kinase inhibitor. The kinase inhibitor can be sorafenib, regorafenib, bortezomib, erlotinib, gefitinib, imatinib, vemurafenib, or vismodegib. For example, the kinase inhibitor can be sorafenib.

In another aspect, this document features methods for identifying a mammal as having a cancer that is responsive to one or more a SCD1 polypeptide inhibitors. The methods can include, or consist essentially of, detecting a level of SCD1 polypeptides within a biological sample from the mammal, detecting a level of cMyc polypeptides within the biological sample from the mammal, and identifying the mammal as having a cancer that is responsive to one or more a SCD1 polypeptide inhibitors when SCD1 polypeptide expression and an elevated level of cMyc polypeptides are detected in the biological sample. The mammal can be a human. The cancer can be liver cancer, renal cell carcinoma, ovarian cancer, breast cancer, prostate cancer, colon cancer, pancreatic cancer, bladder cancer, lung cancer, thyroid cancer, brain cancer, melanoma, or lymphoma. In some cases, the cancer can be liver cancer (e.g., a hepatocellular carcinoma or a cholangiocarcinoma). The method also can include detecting an elevated level of survivin polypeptides within the biological sample from the mammal. The SCD1 polypeptide inhibitor can be a compound having Formula (II) or Formula (IIa):

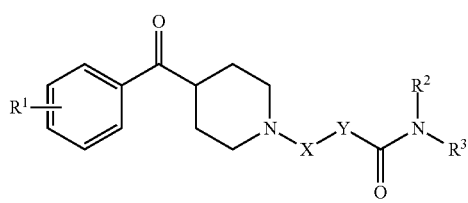

(II)

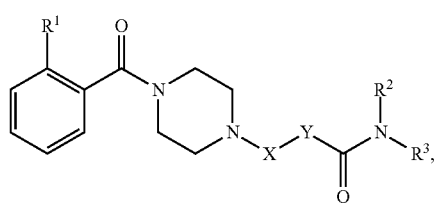

(IIa)

or pharmaceutically acceptable salt thereof, where $R^1$ is halo, X is $-(C=O)NR^4-$, Y is

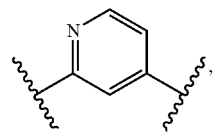

and $R^2$, $R^3$, and $R^4$ are each independently H or an unsubstituted $C_{1-6}$alkyl. In some cases, the SCD1 polypeptide inhibitor can be SSI-4, 2-{[4-(2-Chlorophenoxy)piperidine-1-carbonyl]amino}-N-methylpyridine-4-carboxamide:

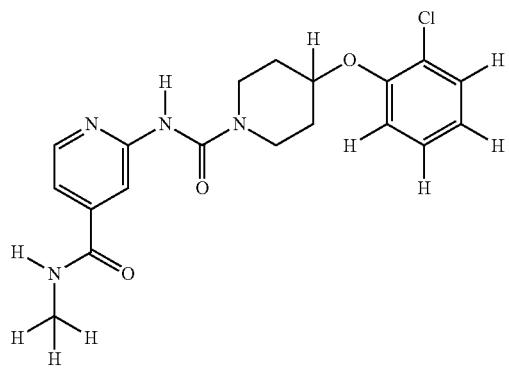 [SMILES: CNC(=O)c1ccnc(NC(=O)N2CCC(Oc3ccccc3Cl)CC2)c1]

or pharmaceutically acceptable salt thereof. The SCD1 polypeptide inhibitor can be a compound having Formula (I) or Formula (Ia):

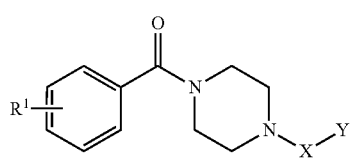

(I)

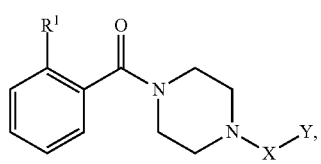

(Ia)

or a pharmaceutically acceptable salt thereof, where $R^1$ is an unsubstituted $C_{1-6}$alkyl or $C_{1-6}$haloalkyl; X is

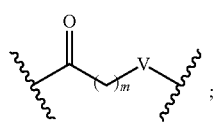

Y is selected from:

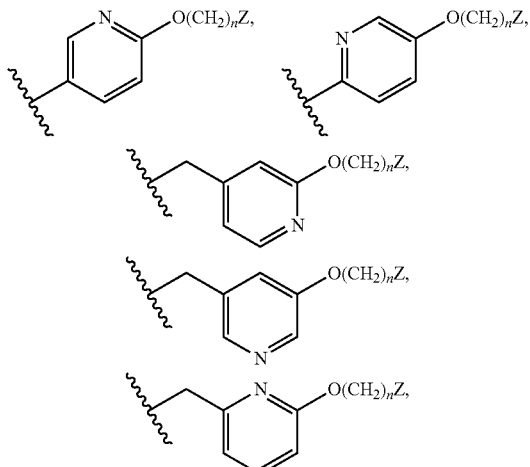

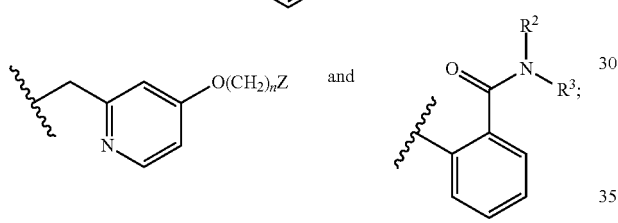

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, the SCD1 polypeptide inhibitor can be SSI-2, 2-(benzyloxy)-5-{[hydroxy({4-[2-(trifluoromethyl)benzoyl]piperazin-1-yl})methyl]amino}-1,2-dihydropyridin-2-ylium-1-ide:

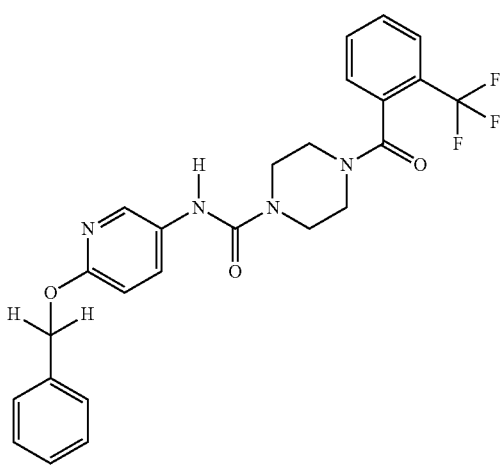 [SMILES: O=C(Nc1ccc(OCc2ccccc2)nc1)N1CCN(C(=O)c2ccccc2C(F)(F)F)CC1]

or pharmaceutically acceptable salt thereof. The method also can include administering an additional therapeutic agent used to treat cancer to the mammal. The additional therapeutic agent can be a chemotherapeutic agent. The chemotherapeutic agent can be a kinase inhibitor. The kinase inhibitor can be sorafenib, regorafenib, bortezomib, erlotinib, gefitinib, imatinib, vemurafenib, or vismodegib. For example, the kinase inhibitor can be sorafenib.

In another aspect, this document features methods for treating a cancer in a mammal. The methods can include, or consist essentially of, identifying the mammal as having a cancer that is responsive to one or more a SCD1 polypeptide inhibitors, where the identifying includes detecting SCD1 polypeptide expression within a biological sample from the mammal and detecting an elevated level of cMyc polypeptides within the biological sample from the mammal, and then administering a SCD1 polypeptide inhibitor to the mammal. The mammal can be a human. The cancer can be liver cancer, renal cell carcinoma, ovarian cancer, breast cancer, prostate cancer, colon cancer, pancreatic cancer, bladder cancer, lung cancer, thyroid cancer, brain cancer, melanoma, or lymphoma. In some cases, the cancer can be liver cancer (e.g., a hepatocellular carcinoma or a cholangiocarcinoma). The method also can include detecting an elevated level of survivin polypeptides within the biological sample from the mammal. The SCD1 polypeptide inhibitor can be a compound having Formula (II) or Formula (IIa):

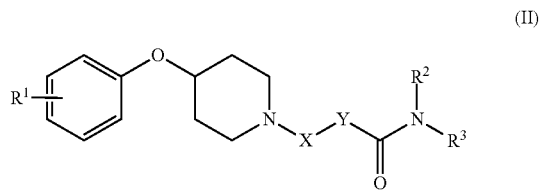

(II)

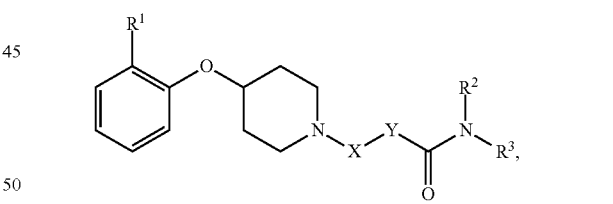

(IIa)

or pharmaceutically acceptable salt thereof, where $R^1$ is halo, X is —(C═O)$NR^4$—, Y is

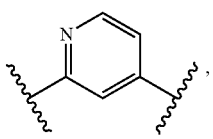 [SMILES: *c1ccnc(*)c1]

and $R^2$, $R^3$, and $R^4$ are each independently H or an unsubstituted $C_{1-6}$alkyl. In some cases, the SCD1 polypeptide inhibitor can be SSI-4, 2-{[4-(2-Chlorophenoxy)piperidine-1-carbonyl]amino}-N-methylpyridine-4-carboxamide:

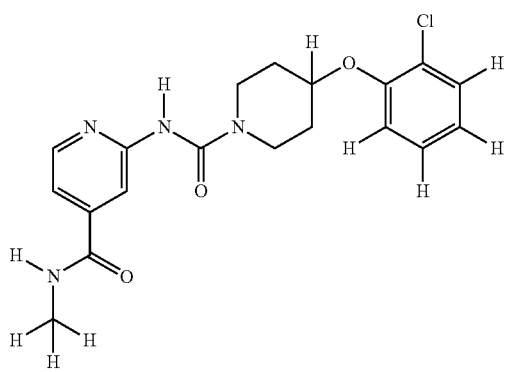 [SMILES: CNC(=O)c1ccnc(NC(=O)N2CCC(Oc3ccccc3Cl)CC2)c1]

or pharmaceutically acceptable salt thereof. The SCD1 polypeptide inhibitor can be a compound having Formula (I) or Formula (Ia):

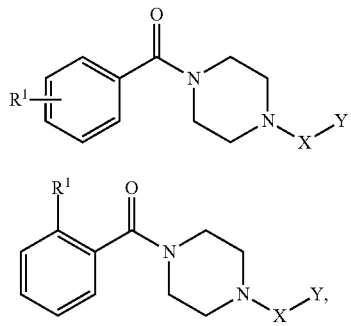

or a pharmaceutically acceptable salt thereof, where $R^1$ is an unsubstituted $C_{1-6}$alkyl or $C_{1-6}$haloalkyl; X is

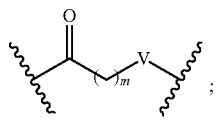

Y is selected from:

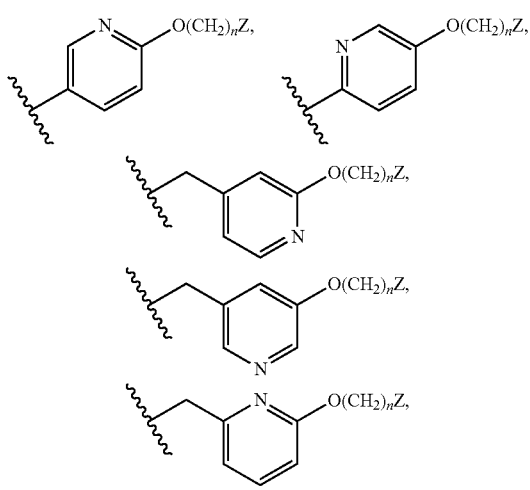

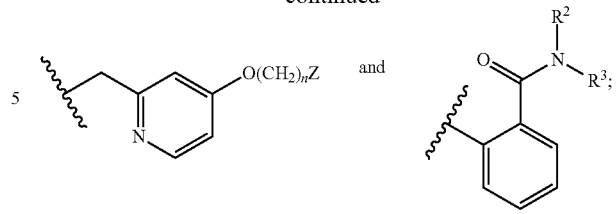

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, the SCD1 polypeptide inhibitor can be SSI-2, 2-(benzyloxy)-5-{[hydroxy({4-[2-(trifluoromethyl)benzoyl]piperazin-1-yl})methyl]amino}-1,2-dihydropyridin-2-ylium-1-ide:

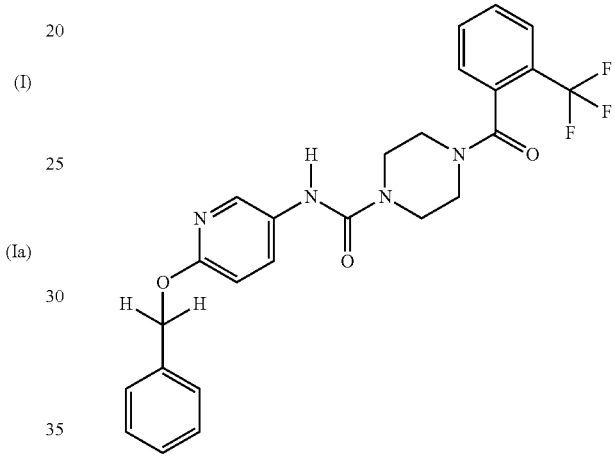

or pharmaceutically acceptable salt thereof. The method also can include administering an additional therapeutic agent used to treat cancer to the mammal. The additional therapeutic agent can be a chemotherapeutic agent. The chemotherapeutic agent can be a kinase inhibitor. The kinase inhibitor can be sorafenib, regorafenib, bortezomib, erlotinib, gefitinib, imatinib, vemurafenib, or vismodegib. For example, the kinase inhibitor can be sorafenib.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1A contains images of SCD1 immunohistochemical (IHC) expression for SCD1 in HCC and CCA. FIG. 1B contains a graph of quantitated SCD1 IHC protein expression in patient tumor tissues for HCC and CCA, and showed that HCC had similar SCD1 expression to that of normal liver tissue while CCA levels were somewhat lower on average. H score is calculated based upon signal intensity (0-3) using the formula: [(1+%×1)+(2+%×2)+(3+%×3)]. * indicates statistical significance (P>0.05).

FIG. 3A contains structures of SSI-4 and SSI-2, two small molecule SCD1 inhibitors. FIG. 3B contains a graph of SCD1 inhibitors evaluated for their inhibition of oleoyl CoA biosynthesis by mouse liver microsomes in vitro. SSI-2 or SSI-4 was incubated with microsomes and 13C18-labeled stearoyl CoA, a native substrate of SCD1. Bioconversion of this substrate to 13C18-labeled oleoyl CoA product was quantified by LC/MS for drug treatments relative to vehicle (DMSO) controls. MF-438, the most active SCD1 inhibitor, is used as a comparator. FIG. 3C contains a graph of mean plasma concentration of SSI-4 following administration of a single dose of oral (PO) or intravenous (IV) SSI-4 to fasted male C57BL/6 mice. Plasma levels were measured over 24 hours. FIG. 3D contains a table of half-life and bioavailability are key parameters measured in the single dose analyses. Bioavailability (%) was calculated with AUC0-last and nominal dose. FIG. 3E contains a full matrix SSI-4 kinome scan. SSI-4 was screened at 10 nM and 100 nM for binding to a total of 468 kinases. Results of SSI-4 kinome scan shown as TREEspot™ chart, where kinases found to bind are marked with red circles. Larger circles indicate higher-affinity binding. Binding to just 1 human atypical kinase (CDKL2) was observed with SSI-4 at a concentration of 100 nM, and to none at 10 nM.

FIG. 4A contains graphs of weight changes in male or female Sprague Dawley rats treated daily with indicated doses of SSI-4 for seven days (n=3 per group). FIG. 4B contains graphs or serum profiles of indicated enzymes measured on day 8 in male or female Sprague Dawley rats treated daily with indicated doses of SSI-4 for seven days (n=3 per group). BUN=blood urea nitrogen; AST=aspartate aminotransferase; ALT=alanine aminotransferase; ALK/Phos=alkaline phosphatase.

FIG. 5A contains a graph of dose responses of 0.01-10 µM SSI-4 with 5 day exposure, and demonstrates IC50 of 1-5 nM. FIG. 5B contains a graph of HCC cell lines demonstrating inhibition of proliferation with 1 µM SSI-4. To demonstrate SCD1 specificity, cells were pretreated with 500 µg/ml of oleic acid to rescue the growth inhibitory phenotype. FIG. 5C contains a graph showing SSI4 responsive HCC cells have decreased unsaturated fatty acids (UFA) after 48 hour SSI4 treatment (black) indicating that the function of SCD1 converting saturated fatty acids to unsaturated fatty acids was inhibited. FIG. 5D contains images of soft agar assays. Single cells grown in 3D soft agar identified SCD1 sensitive cell lines. Only SCD1 sensitive cell lines grew in soft agar. FIG. 5E contains an image of western blot analysis showing that survivin and cMyc were elevated in concert with SCD1 expression in cell lines responsive to SSI-4. FIG. 5F contains images of western blot analyses showing that survivin and cMyc were elevated in concert with SCD1 expression in cell lines responsive to SSI-4. cMyc and survivin are down-regulated with SSI-4 and rescued with oleic acid demonstrating specificity for SCD1. SSI-4 induced apoptosis as evidenced by cleaved PARP with specificity demonstrated by rescue with oleic acid. Endoplasmic reticulum (ER) stress was induced as shown by upregulation of BiP after SSI-4 treatment. Oleic acid blocks upregulation of BiP demonstrating specificity.

FIG. 6A contains IHC images of HCC PDTX models that express equivalent SCD1 and c-Myc with differences in LDHA expression. FIGS. 6B and 6C contains graphs of tumor volume in PAX148 (FIG. 6B) tumor tissues and in LIV58 (FIG. 6C) tumor tissues after treatment with SSI-4. Tumor tissues (5 mm³) with 50% matrigel were implanted in the right flank of 8 week old female athymic nude mice. At ~100 mm3, daily SSI-4 (20-50 mg/kg oral) was begun. Tumor volume and mouse weight were monitored twice weekly. Tumor volume was calculated using (length×width×height/0.523=mm3) and is reported as the mean±S.E. of 10 mice. 20-50 mg/kg demonstrated single agent antitumor activity.

FIG. 7A contains a dose response curve identifying SSI-4 responsive HCC cell lines. FIG. 7B contains a graph demonstrating synergy with combination SSI-4 and sorafenib using Talalay-Chou method for synergy. CI values <1 indicate synergy. FIG. 7C contains a graph showing that combination SSI-4 and sorafenib demonstrated prolonged durable response in a HLE HCC mouse model while single agent sorafenib and SSI-4 escape over time on therapy. FIG. 7D contains a graph demonstrating synergy with combination SSI-4 and regorafenib (an analog of sorafenib) using Talalay-Chou method for synergy. CI values <1 indicate synergy.

FIG. 8A contains a graph of dose responses of 0.1-1 µM SSI-4 with 5 day exposure in CCA cell lines. FIG. 8B contains a graph of CCA cell lines demonstrating inhibition of proliferation with 1 µM SSI-4. To demonstrate SCD1 specificity, cells were pretreated with 500 µg/ml of oleic acid to rescue the growth inhibitory phenotype. FIG. 8C contains graph of tumor volume in CX-003 CCA tumor tissues after treatment with SSI-4. Tumor tissues (5 mm³) with 50% matrigel were implanted in the right flank of 8 week old female athymic nude mice. At ~100 mm3, daily SSI-4 (50 mg/kg oral) was begun. Tumor volume and mouse weight were monitored twice weekly. Tumor volume was calculated using (length×width×height/0.523=mm3) and is reported as the mean±S.E. of 10 mice. 50 mg/kg showed no response to SSI-4 treatment in a c-Myc negative CCA model.

DETAILED DESCRIPTION

Figure 1A:
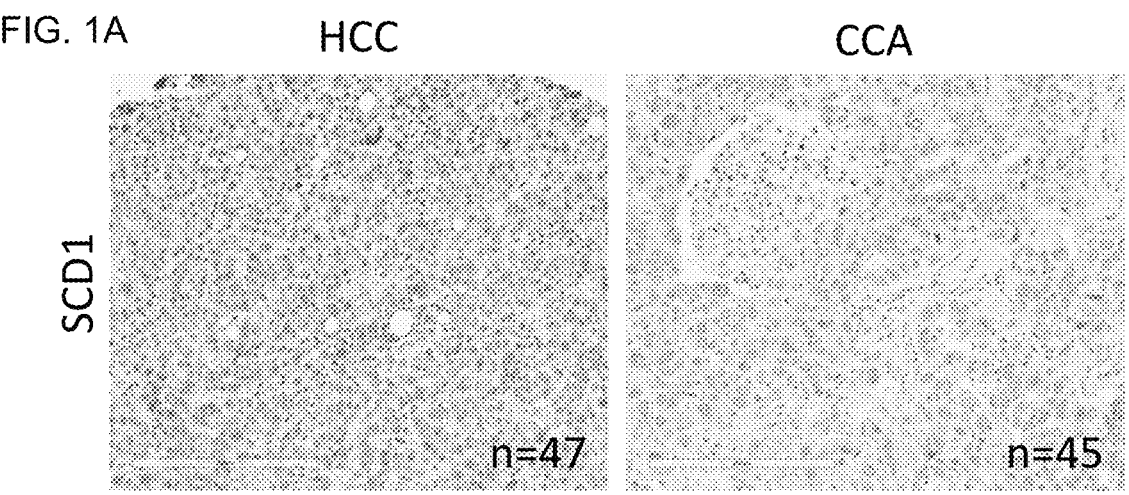
FIGS. 1A-1B show that SCD1 protein is expressed in hepatocellular carcinoma (HCC) and cholangiocarcinoma (CCA) patient tissues.

SCD1 is an enzyme that catalyzes the de novo lipogenesis of Δ-9 monounsaturated fatty acids (MUFA) oleic acid (OA) and palmitoleic acid (PA). These MUFAs are essential for the synthesis of triglycerides, sphingolipids, ceramides, glycolipids, phospholipids, and other lipoproteins which influence membrane fluidity, membrane raft formation and receptor clustering, second messenger signaling, fatty acid oxidation, energy storage, cell division, inflammation, and a number of other biological functions (Guillou et al., 2010 *Prog Lipid Res.* 49(2):186-199). Aberrant upregulation of SCD1 has been implicated in the development of certain types of cancer; however, not all SCD1-associated cancers are responsive to SCD1 polypeptide inhibitors. As used herein, a cancer associated with expression (e.g., overexpression) of a SCD1 polypeptide can also be referred to as a SCD1-associated cancer (see, e.g., von Roemeling et al. 2015 *J. Clin. Endocrinol. Metab.* 100:E697-E709). As described herein, the presence of elevated levels of one or more Wnt regulated polypeptides, such as cMyc and survivin, in a SCD1-associated cancer can indicate that the SCD1-associated cancer is likely to be responsive to treatment with one or more SCD1 polypeptide inhibitors (e.g., SSI-4).

This document provides methods and materials for diagnosing (or identifying as having) mammals (e.g., humans) having cancer (e.g., a SCD1-associated cancer). For example, the methods and materials described herein can be used to diagnose a mammal as having a SCD1-associated cancer. In some cases, a mammal having a cancer can be assessed to determine whether the cancer is a SCD1-associated cancer. Any appropriate method can be used to identify a mammal having cancer. For example, imaging techniques and biopsy techniques can be used to identify mammals (e.g., humans) having cancer. In some cases, the presence, absence, or level of SCD1 polypeptides can be detected in a sample (e.g., a biological sample) obtained from a mammal to determine if mammal has a SCD1-associated cancer. For example, when the presence of an elevated level of SCD1 polypeptides is detected, the mammal can be identified as having a SCD1-associated cancer.

This document also provides methods and materials for assessing mammals (e.g., humans) having a cancer (e.g., a SCD1-associated cancer). A mammal identified as having a SCD1-associated cancer can be assessed to determine whether or not the SCD1-associated cancer will respond to treatment (e.g., treatment with one or more SCD1 polypeptide inhibitors). In some cases, the presence, absence, or level of one or more Wnt regulated polypeptides can be detected in a sample (e.g., a biological sample) obtained from a mammal to determine the responsiveness of the cancer to a treatment. The presence of an elevated level of one or more Wnt regulated polypeptides (e.g., cMyc and/or survivin) can indicate that a SCD1-associated cancer is responsive to one or more SCD1 polypeptide inhibitors. For example, when the presence of an elevated level of one or more Wnt regulated polypeptides is detected in a sample obtained from a mammal having a SCD1-associated cancer, the mammal can be identified as having a SCD1-associated cancer that is likely to be responsive to one or more SCD1 polypeptide inhibitors. A SCD1-associated cancer that is likely to be responsive to one or more SCD1 polypeptide inhibitors can include elevated levels of one or more (e.g., one, two, three, four, five, or more) Wnt regulated polypeptides. The Wnt regulated polypeptides can be any appropriate Wnt regulated polypeptides. In some cases, a Wnt regulated polypeptide can be associated with promoting cell proliferation (e.g., cMyc and cyclin D1). In some cases, a Wnt regulated polypeptide can be associated with cell survival (e.g., survivin). Examples of Wnt regulated polypeptides include, without limitation, cMyc, survivin, and cyclin D1. In some cases, a SCD1-associated cancer that is likely to be responsive to one or more SCD1 polypeptide inhibitors includes elevated levels of cMyc polypeptides. In some cases, a SCD1-associated cancer that is likely to be responsive to one or more SCD1 polypeptide inhibitors includes elevated levels of cMyc polypeptides and elevated levels of survivin polypeptides.

The term "elevated level" as used herein with respect to a level of one or more Wnt regulated polypeptides (e.g., cMyc and/or survivin) refers to any level that is greater than a reference level of one or more Wnt regulated polypeptides, respectively. The term "reference level" as used herein with respect to one or more Wnt regulated polypeptides refers to the level of one or more Wnt regulated polypeptides typically observed in a sample (e.g., a control sample) from one or more mammals (e.g., humans) without cancer. Control samples can include, without limitation, samples from normal (e.g., healthy) mammals, and cell lines (e.g., non-tumor forming cells lines). In some cases, an elevated level of one or more Wnt regulated polypeptides can be a level that is about least 2 (e.g., at least 3, at least 4, at least 5, at least 6, at least 7, at least 8, at least 9, or at least 10) fold greater relative to a reference level of one or more Wnt regulated polypeptides. In some cases, when control samples have undetectable levels of one or more Wnt regulated polypeptides, an elevated level can be a detectable level of one or more Wnt regulated polypeptides. It will be appreciated that levels from comparable samples are used when determining whether or not a particular level is an elevated level.

Any appropriate sample can be used to detect an elevated level of one or more Wnt regulated polypeptides (e.g., cMyc and/or survivin). In some cases, a sample can be a tumor sample (e.g., a biopsy). In some cases, a sample can be a biological sample. For example, biological samples such as tissue samples (e.g., liver tissue) and/or fluids (e.g., blood, serum, plasma, or urine) can be obtained from a mammal and assessed for the presence of one or more Wnt regulated polypeptides. In some cases, a liver tissue sample can be used as a biological sample to determine whether or not the mammal has an elevated level of one or more Wnt regulated polypeptides.

Any appropriate method can be used to detect the presence, absence, or level of one or more Wnt regulated polypeptides (e.g., cMyc and/or survivin) within a sample (e.g., a biological sample). For example, immunohistochemistry (IHC) techniques, mass spectrometry techniques (e.g., proteomics-based mass spectrometry assays or targeted quantification-based mass spectrometry assays), western blotting techniques, and quantitative RT-PCR techniques can be used to determine whether or not a sample contains an elevated level of one or more Wnt regulated polypeptides. In some cases, IHC and/or western blotting techniques can be used to determine whether or not a particular sample contains an elevated level of one or more Wnt regulated polypeptides.

This document also provides methods and materials for treating mammals (e.g., humans) diagnosed with (or identified as having) a cancer as described herein (e.g., a SCD1-associated cancer) and/or identified as having a SCD1-associated cancer that is likely to be responsive to one or more SCD1 polypeptide inhibitors by administering one or more SCD1 polypeptide inhibitors. In some cases, the methods and materials described herein can be used to treat a mammal having a cancer exhibiting an elevated level of a SCD1 polypeptides. In some cases, the methods and materials described herein can be used to treat a mammal having a cancer exhibiting an elevated level of a SCD1 polypeptides and an elevated level of cMyc polypeptides.

Once identified as having a cancer SCD1-associated cancer and/or as having a SCD1-associated cancer that is likely to be responsive to one or more SCD1 polypeptide inhibitors, a mammal can be administered or instructed to self-administer one or more SCD1 polypeptide inhibitors (e.g., one, two, three, four, five, or more SCD1 inhibitors). In some cases, the methods and materials described herein can include identifying a mammal as having a cancer (e.g., a SCD1-associate cancer). In some cases, the methods and materials described herein can be used to treat a mammal identified (e.g., previously identified) as having cancer (e.g., a SCD1-associate cancer).

Administration of a SCD1 polypeptide inhibitor to a mammal having an elevated level of SCD1 polypeptides can be effective to treat cancer (e.g., cancer having an elevated level of SCD1 polypeptides and an elevated level of Wnt regulated polypeptides). In some cases, treating a mammal as described herein can be effective to slow or prevent growth of a cancer. For example, administering one or more SCD1 polypeptide inhibitors to a mammal identified as having a SCD1-associated cancer and/or identified as having a SCD1-associated cancer that is likely to be responsive to one or more SCD1 polypeptide inhibitors can be effective to prevent a tumor from increasing in size (e.g., volume). For example, administering one or more SCD1 polypeptide inhibitors to a mammal identified as having a SCD1-associated cancer and/or identified as having a SCD1-associated cancer that is likely to be responsive to one or more SCD1 polypeptide inhibitors can be effective prevent a tumor from metastasizing. In some cases, treating a mammal as described herein can be effective to reduce or eliminate the number of cancer cells within the mammal. For example, administering one or more SCD1 polypeptide inhibitors to a mammal identified as having a SCD1-associated cancer and/or identified as having a SCD1-associated cancer that is likely to be responsive to one or more SCD1 polypeptide inhibitors can be effective to reduce the size (e.g., volume) of a tumor. In some cases, treating a mammal as described herein can be effective to induce endoplasmic reticulum (ER) stress in cancer cells within the mammal. In some cases, treating a mammal as described herein can be effective to induce apoptotic cell death of cancer cells within the mammal.

Any type of mammal can be assessed and/or treated as described herein. Examples of mammals that can be assessed and/or treated as described herein include, without limitation, primates (e.g., humans and monkeys), dogs, cats, horses, cows, pigs, sheep, rabbits, mice, and rats. In some cases, the mammal can be a human. For example, humans identified as having a SCD1-associated cancer and/or identified as having a SCD1-associated cancer that is likely to be responsive to one or more SCD1 polypeptide inhibitors can be treated with one or more SCD1 polypeptide inhibitors as described herein.

When treating a mammal (e.g., human) identified as having a cancer as described herein and/or identified as having a cancer that is responsive to one or more SCD1 polypeptide inhibitors as described herein, the cancer can be any cancer. In some cases, the cancer can be a SCD1-associated cancer. A cancer can be a primary cancer or a metastatic cancer. In some cases, a cancer can be a cancer that has escaped and/or has been non-responsive to chemotherapy (e.g., a chemoresistant cancer). Examples of cancers that can be treated as described herein include, without limitation, liver cancer (e.g., HCC and/or CCA), renal cell carcinoma, ovarian cancer, breast cancer, prostate cancer, colon cancer, pancreatic cancer, bladder cancer, lung cancer, thyroid cancer, brain cancer, melanoma, and lymphoma. In some cases, a cancer treated as described herein can be a HCC. In some cases, a cancer treated as described herein can be a CCA.

When treating a mammal (e.g., human) identified as having cancer as described herein and/or identified as having a cancer that is responsive to one or more SCD1 polypeptide inhibitors as described herein, any appropriate SCD1 polypeptide inhibitor can be administered to the mammal. A SCD1 polypeptide inhibitor can be any appropriate type of molecule (e.g., nucleic acid molecules designed to induce RNA interference (e.g., a siRNA molecule or a shRNA molecule), antisense molecules, miRNAs, and antibodies (e.g., antibodies (e.g., monoclonal antibodies)) that can reduce or eliminate SCD1 polypeptide expression or SCD1 polypeptide function. A SCD1 polypeptide inhibitor can be an inhibitor of SCD1 polypeptide expression or an inhibitor of SCD1 polypeptide activity. In some cases, a SCD1 polypeptide inhibitor can be readily designed based upon the nucleic acid and/or polypeptide sequences of SCD1. In some cases, a SCD1 polypeptide inhibitor can be as described elsewhere (see, e.g., WO 2016/022955). In some cases, a SCD1 polypeptide inhibitor can have Formula (I):

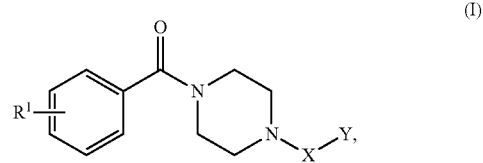

(I)

or a pharmaceutically acceptable salt thereof, where $R^1$ is an unsubstituted $C_{1-6}$alkyl or $C_{1-6}$haloalkyl; X is

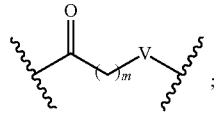

;

Y is selected from:

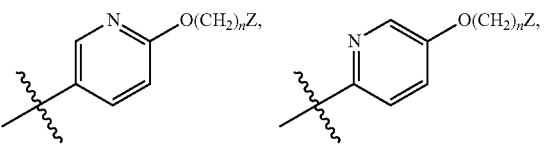

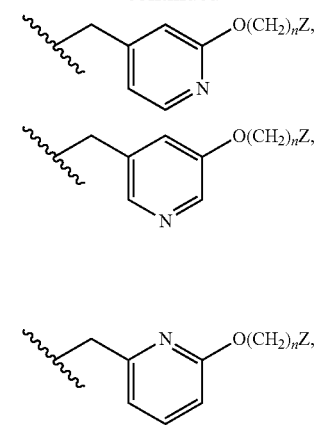

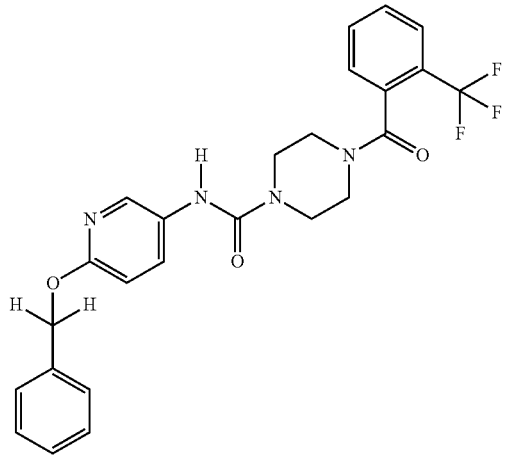 [SMILES: O=C(Nc1ccc(OCc2ccccc2)nc1)N1CCN(C(=O)c2ccccc2C(F)(F)F)CC1]

SSI-2, 2-(benzyloxy)-5-{[hydroxy({4-[2-(trifluoromethyl)benzoyl]piperazin-1-yl})methyl]amino}-1,2-dihydropyridin-2-ylium-1-ide; and

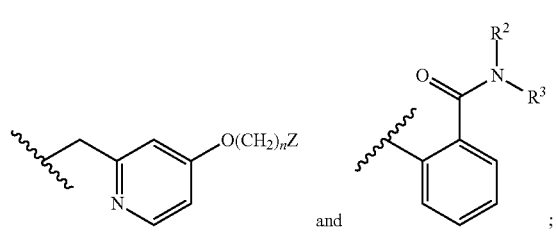

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, a SCD1 polypeptide inhibitor according to Formula (I) can have the structure of Formula (Ia):

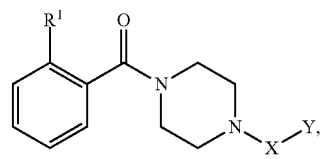

(Ia)

or a pharmaceutically acceptable salt thereof. Representative examples of SCD1 polypeptide inhibitors according to Formula (I) and/or Formula (Ia) include, without limitation:

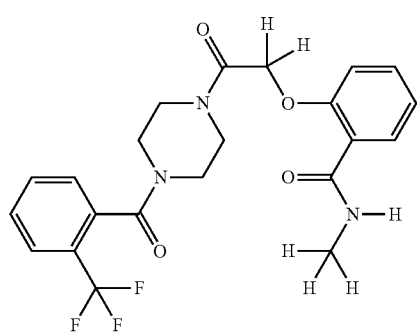 [SMILES: CNC(=O)c1ccccc1OCC(=O)N1CCN(C(=O)c2ccccc2C(F)(F)F)CC1]

SSI-1, N-Methyl-2-(2-oxo-2-{4-[2-(trifluoromethyl)benzoyl]piperazin-1-yl}ethoxy)benzamide;

SSI-3, 2-(benzyloxy)-4-({[hydroxy({4-[2-(trifluoromethyl)benzoyl]piperazin-1-yl})methyl]azanidyl}methyl)-1,2-dihydropyridin-2-ylium-1-ide, or a pharmaceutically acceptable salt thereof. In some cases, a SCD1 polypeptide inhibitor can have Formula (II):

(II)

or pharmaceutically acceptable salt thereof, where $R^1$ is halo; X is —(C=O)$NR^4$—; Y is

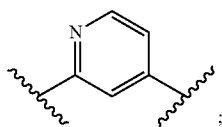 [SMILES: *c1ccnc(*)c1]

$R^2$, $R^3$, and $R^4$ are each independently H or an unsubstituted $C_{1-6}$alkyl.

In some cases, a SCD1 polypeptide inhibitor according to Formula (II) can have the structure of Formula (IIa):

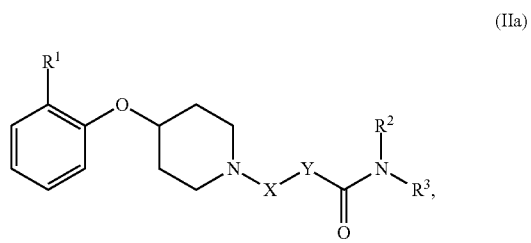

(IIa)

or pharmaceutically acceptable salt thereof. A representative example of a SCD1 polypeptide inhibitor according to Formula (II) and/or Formula (IIa) include:

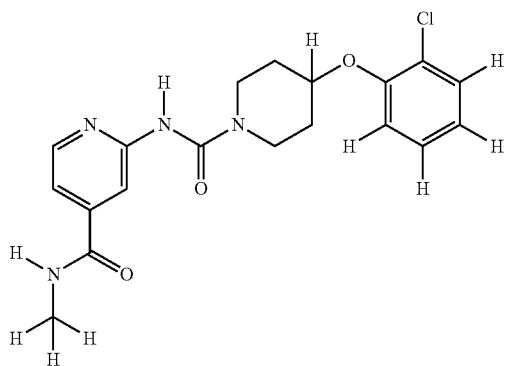 [SMILES: CNC(=O)c1ccnc(NC(=O)N2CCC(Oc3ccccc3Cl)CC2)c1]

SSI-4, 2-{[4-(2-Chlorophenoxy)piperidine-1-carbonyl]amino}-N-methylpyridine-4-carboxamide, or pharmaceutically acceptable salt thereof. In some cases, a SCD1 polypeptide inhibitor can be SSI-4.

In some cases, one or more SCD1 polypeptide inhibitors can be administered to a mammal (e.g., human) identified as having cancer (e.g., a SCD1-associate cancer) as described herein and/or identified as having a cancer that is likely to be responsive to one or more SCD1 polypeptide inhibitors as described herein as the sole anti-cancer treatment agent. For example, SSI-4 can be administered to a mammal identified as having a SCD1-associate cancer as described herein and/or identified as having a cancer that is likely to be responsive to one or more SCD1 polypeptide inhibitors as described herein as the sole anti-cancer treatment agent.

In some cases, when treating a mammal (e.g., human) identified as having cancer (e.g., a SCD1-associate cancer) and/or identified as having a cancer that is likely to be responsive to one or more SCD1 polypeptide inhibitors as described herein, the mammal also can be administered or instructed to self-administer one or more additional therapeutic agents (e.g., therapeutic agents used to treat cancer). In some cases, the one or more additional therapeutic agents can include agents approved by the Food and Drug Administration (FDA) for a particular type of cancer. For example, in cases where the mammal has a liver cancer, the one or more additional therapeutic agents can include agents approved by the FDA for liver cancer. Examples of therapeutic agents that can be used to treat cancer include, without limitation, radiation therapy; surgery; and chemotherapeutic agents (including, but not limited to, alkylating agents (e.g., cyclophosphamide, mechlorethamine, chlorambucil, melphalan, dacarbazine, nitrosoureas, temozolomide), anthracyclines (e.g., daunorubicin, doxorubicin, epirubicin, idarubicin, mitoxantrone, and valrubicin), cytoskeletal disruptors (e.g., paclitaxel, docetaxel, abraxane, and taxotere), histone deacetylase inhibitors (e.g., vorinostat and romidepsin), topoisomerase inhibitors (e.g., irinotecan, topotecan, etoposide, teniposide, and tafluposide), kinase inhibitors (e.g., sorafenib, regorafenib, bortezomib, erlotinib, gefitinib, imatinib, vemurafenib, and vismodegib), nucleotide analogs and precursor analogs (e.g., azacitidine, azathioprine, capecitabine, cytarabine, doxifluridine, fluorouracil, gemcitabine, hydroxyurea, mercaptopurine, methotrexate, and tioguanine), peptide antibiotics (e.g., bleomycin and actinomycin), platinum-based agents (e.g., carboplatin, cisplatin, and oxaliplatin), retinoids (e.g., tretinoin, alitretinoin, and bexarotene), and vinca alkaloids and derivatives (e.g., vinblastine, vincristine, vindesine, and vinorelbine)). For example, one or more SCD1 polypeptide inhibitors can be administered in combination with sorafenib to a mammal (e.g., human) identified as having a SCD1-associated cancer and/or identified as having a cancer that is likely to be responsive to one or more SCD1 polypeptide inhibitors to treat the mammal. In cases where one or more SCD1 polypeptide inhibitors described herein are used in combination with one or more therapeutic agents to treat cancer, the one or more SCD1 polypeptide inhibitors can be administered at the same time or independently of the administration of one or more therapeutic agents. For example, the composition including one or more SCD1 polypeptide inhibitors can be administered before, concurrent with, or after the one or more therapeutic agents are administered.

In some cases, one or more SCD1 polypeptide inhibitors (e.g., SSI-4) can be administered to a mammal (e.g., a mammal identified as having a SCD1-associated cancer and/or identified as having a cancer that is likely to be responsive to one or more SCD1 polypeptide inhibitors) once or multiple times over a period of time ranging from days to weeks. In some cases, one or more SCD1 polypeptide inhibitors described herein can be formulated into a pharmaceutically acceptable composition for administration to a mammal. For example, a therapeutically effective amount of one or more SCD1 polypeptide inhibitors can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more SCD1 polypeptide inhibitors (e.g., SSI-4) can be designed for oral, parenteral (including subcutaneous, intramuscular, intravenous, and intradermal), or intratumoral administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more SCD1 polypeptide inhibitors (e.g., SSI-4) can be administered locally (e.g., intratumorally) or systemically. For example, a composition provided herein can be administered locally by injection into tumors or into biological spaces infiltrated by tumors (e.g. peritoneal cavity and/or pleural space). In some cases, a composition provided herein can be administered systemically, orally, or by injection to a mammal (e.g., a human).

Effective doses can vary depending on the risk and/or the severity of the cancer, the route of administration, the age and general health condition of the mammal, excipient usage, the possibility of co-usage with other therapeutic treatments such as use of other agents, and the judgment of the treating physician.

An effective amount of a composition containing one or more SCD1 polypeptide inhibitors (e.g., SSI-4) can be any amount that reduces the number of cancer cells present within the mammal without producing significant toxicity to the mammal. In some cases, an effective amount of one or more SCD1 polypeptide inhibitors can be from about 10 to about 100 mg per kg body weight (mg/kg) of the mammal being treated. For example, an effective amount of one or more SCD1 polypeptide inhibitors can be from about 10 to about 90, from about 10 to about 80, from about 10 to about 70, from about 10 to about 60, from about 10 to about 50, from about 10 to about 40, from about 10 to about 30, from about 20 to about 100, from about 30 to about 100, from about 40 to about 100, from about 50 to about 100, from about 60 to about 100, from about 70 to about 100, from about 80 to about 100, from about 15 to about 90, from about 20 to about 80, from about 25 to about 75, from about 30 to about 60, from about 35 to about 50, or from about 40 to about 50 mg/kg of the mammal being treated. In some cases, about 30 mg/kg of one or more SCD1 polypeptide inhibitors can be administered (e.g., orally administered) to a human identified as having a SCD1-associated cancer as described herein and/or identified as having a cancer that is likely to be responsive to one or more SCD1 polypeptide inhibitors as described herein. In some cases, about 50 mg/kg of one or more SCD1 polypeptide inhibitors can be administered (e.g., orally administered) to a human identified as having a SCD1-associated cancer as described herein and/or identified as having a cancer that is likely to be responsive to one or more SCD1 polypeptide inhibitors as described herein. In some cases, about 100 mg/kg of one or more SCD1 polypeptide inhibitors can be administered (e.g., orally administered) to a human identified as having a SCD1-associated cancer as described herein and/or identified as having a cancer that is likely to be responsive to one or more SCD1 polypeptide inhibitors as described herein.

If a particular mammal fails to respond to a particular amount, then the amount of one or more SCD1 polypeptide inhibitors (e.g., SSI-4) can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more SCD1 polypeptide inhibitors (e.g., SSI-4) can be any amount that reduces the number of cancer cells present within the mammal without producing significant toxicity to the mammal. For example, the frequency of administration of one or more SCD1 polypeptide inhibitors can be from about two to about three times a week to about two to about three times a month. In some cases, a mammal identified as having a SCD1-associated cancer and/or identified as having a cancer that is likely to be responsive to one or more SCD1 polypeptide inhibitors can receive a single administration of one or more SCD1 polypeptide inhibitors described herein. The frequency of administration of one or more SCD1 polypeptide inhibitors described herein can remain constant or can be variable during the duration of treatment. A course of treatment with a composition containing one or more SCD1 polypeptide inhibitors described herein can include rest periods. For example, a composition containing one or more SCD1 polypeptide inhibitors described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more SCD1 polypeptide inhibitors (e.g., SSI-4) can be any duration that reduces the number of cancer cells present within the mammal without producing significant toxicity to the mammal. In some cases, the effective duration can vary from several months to several years. In general, the effective duration for reducing the number of cancer cells present within the mammal can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, the number of cancer cells present within a mammal can be monitored. Any appropriate method can be used to determine whether or not the number of cancer cells present within a mammal is reduced. For example, imaging techniques can be used to assess the number of cancer cells present within a mammal.

The invention will be further described in the following examples, which do not limit the scope of the invention described in the claims.

EXAMPLES

Example 1: Targeting Stearoyl CoA Desaturase 1 (SCD1) in Hepatocellular Carcinoma Antitumor activity of SCD1 inhibitor, SSI-4, against HCC in cell culture and animal models for HCC was shown. SSI-4 also exhibited synergy with sorafenib, an FDA approved drugs for HCC.

Methods

Small Molecule SCD1 Inhibitors

To target SCD1, small molecule SCD1 inhibitors were developed through a combined computational and synthetic chemistry approach as described elsewhere (see, e.g., WO 2016/022955). Using combined computational and synthetic chemistry approaches, we synthesized four novel specific SCD1 inhibitors with SSI-4 being the lead SCD1 inhibitor.

Toxicity Tests

Sprague dawley rats (6-8 weeks old M/F) were orally gavaged with SS1-4 at the indicated dose daily, for a duration of seven days. For each dose levels 3 male and 3 females were placed on study. Rats were clinically observed and weighed daily. On day 8 rats were euthanatized and blood was collected by cardiac puncture. Blood chemistry was measured by STAT Veterinary laboratory.

Preclinical Pharmacokinetics

Pharmacokinetic assessment was performed for SSI-4 administered to fasted male C57BL/6 mice either intravenously (IV) or by oral gavage (PO) in DMSO:PEG400:water (10:70:20) as a clear solution at 5 mg/mL (IV dosing), and 1.3 or 10 mg/mL (respectively for the PO dosing). Serum analysis was performed by LC-MS-MS. PK calculation settings were obtained using the Phoenix WinNonlin 6.3 program, using either the Noncompartmental model 201 (IV bolus input) or Noncompartmental model 200 (extravascular input). Microsomes were isolated from murine liver using Microsome Isolation Kit (BioVision). Each assay (100 µL) contained 50 µg of microsomes, 1 µL of DMSO (for no drug controls) or DMSO-solubilized SCD1 inhibitor, 1 mM reduced NADH, 60 □M coenzyme A, 1 mM ATP, 1 mM DTT, and 5 mM MgCl2 in 100 mM sodium phosphate buffer (pH 7.4). Assays were incubated for five minutes at 25 C and then supplemented with 30 µM 13C18-stearoyl CoA lithium salt to initiate SCD1-catalyzed conversion to 13C18-oleoyl CoA. Following incubation at 37 C for 30 min, enzymes were inactivated and precipitated by adding two volumes (200 µL) of acetonitrile and samples supplemented with 1 µM heptadecaonyl CoA internal standard (I.S.) for LC/MS analyses. Samples were centrifuged at 13,000 rpm for 10 min. To quantify biotransformation of 13C18-stearoyl CoA to 13C18-oleoyl CoA for drug treatments relative to vehicle controls, supernatants were evaluated using the LC/MS2 acyl CoA quantitation method of Magnes et al. and adapting selected reaction monitoring (SRM) for isotope-labeled acyl CoAs. LC/MS2 was conducted using a Thermo LTQ mass spectrometer interfaced with a Dionex UltiMate 8000 LC system. SRM signal areas for isotope-labeled acyl CoAs were measured relative to the heptadecanoyl CoA I.S. using XCalibur software, and percent enzyme inhibition determined by comparing 13C18-oleoyl CoA quantities between treatment and DMSO control assays. Dose-response curves were prepared using GraphPad Prism.

Kinome Scan

Kinome Scan was conducted by Lead Hunter Discovery Services

Xenograft (PDTX) Mouse Models

Tissues were cut into 4×4×4 mm cubes and surgically implanted under anesthesia with 100 µl Matrigel into 4-6 week old athymic nude female mice. Tumors were measured 1 to 2 times per week using calipers and volumes calculated by 0.536*(L×W×H). Once tumors reached ~100 mm3, either placebo or SSI-4 treatment was administered at 180, or 600 mg/kg in custom AIN76 animal chow by Research Diets, Inc. Based upon food consumption, the amount of SSI4 ingested was 20 mg/kg and 50 mg/kg, respectively. For the combination study, mice were administered either 10 mg/kg SSI4, 30 mg/kg sorafenib or both in Nutra-gel diet.

Immunohistochemistry

FFPE tissues were cut into 5 µm sections, deparaffinized, hydrated, antigen retrieved for 25 minutes at pH 6.0 and blocked for 5 minutes with Dako diluent. Immunostaining was done for 1 hour with either lamin A+C, SCD1, c-Myc, survivin, LDHA, ki67, and BIP primary antibodies. For detection, the Envision Dual Labeled Polymer kit (Dako) was used for 30 minutes for anti-species secondary antibodies and stained with DAB chromagen for 5 minutes. Then, lightly counterstained with Gill I hematoxylin for 30 seconds before dehydration and mounting. Images were obtained at 20× using an Aperio AT2 Scanscope. IHC scoring was done using an algorithm in the Imagescope software based upon signal intensity of weak (1+), moderate (2+) or strong staining (3+) with criteria of at least 20% positivity. H score was calculated based upon signal intensity (0-3) using the formula: [(1+%×1)+(2+%×2)+(3+%×3)].

Proliferation Assays

Cell lines were maintained in DMEM media supplemented with sodium pyruvate, HEPES, non-essential amino acids, 3% FBS and antibiotics. Cells were plated at 30,000 cells per well in 12-well plate and treated for 4-5 days at the indicated doses with SSI4 and sorafenib diluted in DMSO at 1:1000. Cell number was determined by using a Coulter Particle Counter.

Lipid Assays

Cells were treated for 48 hours with 1 µM SSI4 and lipids from 8 million cells were extracted using the 1957 Folch Lipid Extraction method. Lipids were re-suspended in DMSO and analyzed using Cell Biolab's lipid quantitation assay kit. Borosilicate glass tubes and polypropylene tips were used during the experiments. Samples were read at OD540 nm and were background corrected on a Spectramax M3 spectrophotometer.

Soft Agar Assays

Soft agar cultures were prepared by diluting 2× growth medium 1:1 in 1.5% Seaplaque GTG agarose with 1000 cells/plate in 6-well culture dishes. Colonies were stained with Giemsa after 3 weeks and colonies larger than 150 µm were counted using Image J software.

Western Blot Analysis

Cells were collected via scraping and lysed in RIPA extraction buffer containing protease inhibitor cocktail and phosphatase inhibitor. Protein concentrations were measured by bicinchoninic acid (BCA) assay and 30 µg were loaded on 4-12% Bis-Tris/MES gels and then transferred to 0.2 µm Immobilon-P membranes. The membranes were hybridized overnight at 4° C. with the following antibodies: SCD1, PARP, survivin, c-Myc, BIP and β-actin. Secondary species-specific horseradish peroxidase-labeled antibodies were from Jackson Immunoresearch. Detection was performed using Supersignal chemiluminescence kit.

Lentiviral Infection

Self-inactivating shRNA lentiviruses were generated using MISSION shRNA pLKO.1 constructs that included a nontarget control which was a random scrambled sequence (SHC002) and c-Myc 1657 (clone NM_002467.2-1657s1c1). Lentiviruses were packaged using 293FT cells via transfection of the pLKO.1 constructs along with packaging plasmids using OptiMEM and Lipofectamine 2000. The packaging plasmids were originally made by Didier Trono supplied by Addgene, which included: pMDLg/pRRE (gag/pol) (plasmid #12251), pRSV-Rev (plasmid #12253), and pMD2.G (VSVG) (plasmid #12259). Supernatants were collected 72 h post-transfection, passed through a 0.45 μm PVDF syringe filter and applied to cells for infection along with 5 μg/ml polybrene. Cells were selected with puromycin.

qPCR

Confluent 10-cm plates were scraped and pelleted. RNA was isolated using Purelink® RNA minikits. Two-step quantitative reverse transcriptase-mediated real-time PCR (qPCR) was used to measure changes in mRNA levels. The RT step was achieved by synthesizing cDNA using the High Capacity Reverse Transcription kit. The PCR step was done using TaqMan® Fast Universal PCR Master Mix and TaqMan® FAM™ dye-labeled probes for c-Myc, LDHA and POLR2A (Hs00172187_m1). Data was normalized to POLR2A for each sample. Fold change values between nontargets and shRNA samples were calculated using the ΔΔCt method (Schmittgen and Livak 2008).

Results

SCD1 Expression in Liver Cancers

Figure 1B:
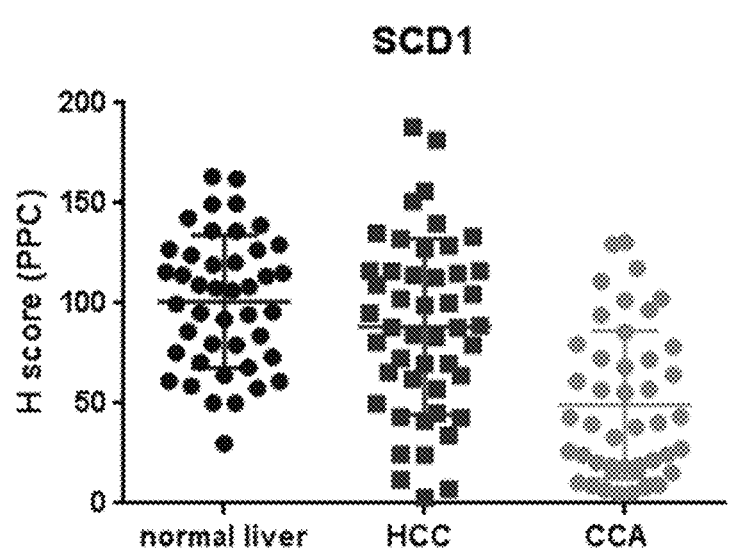
Figure 2A:
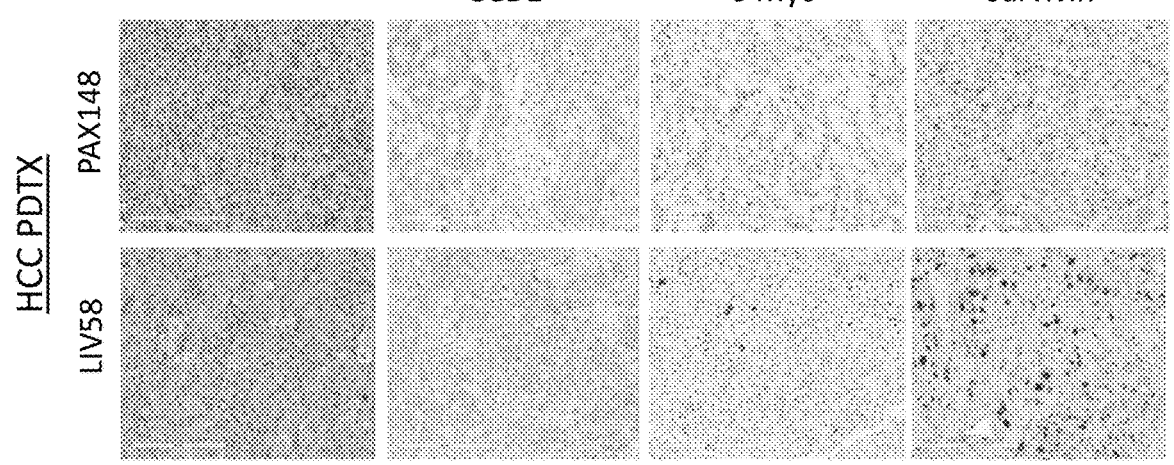
FIGS. 2A-2B contain images of IHC detection of SCD1, cMyc, and survivin proteins expressed in HCC patient derived xenograft (PDTX) tissues (FIG. 2A) and CCA PDTX tissues (FIG. 2B).
Figure 2B:
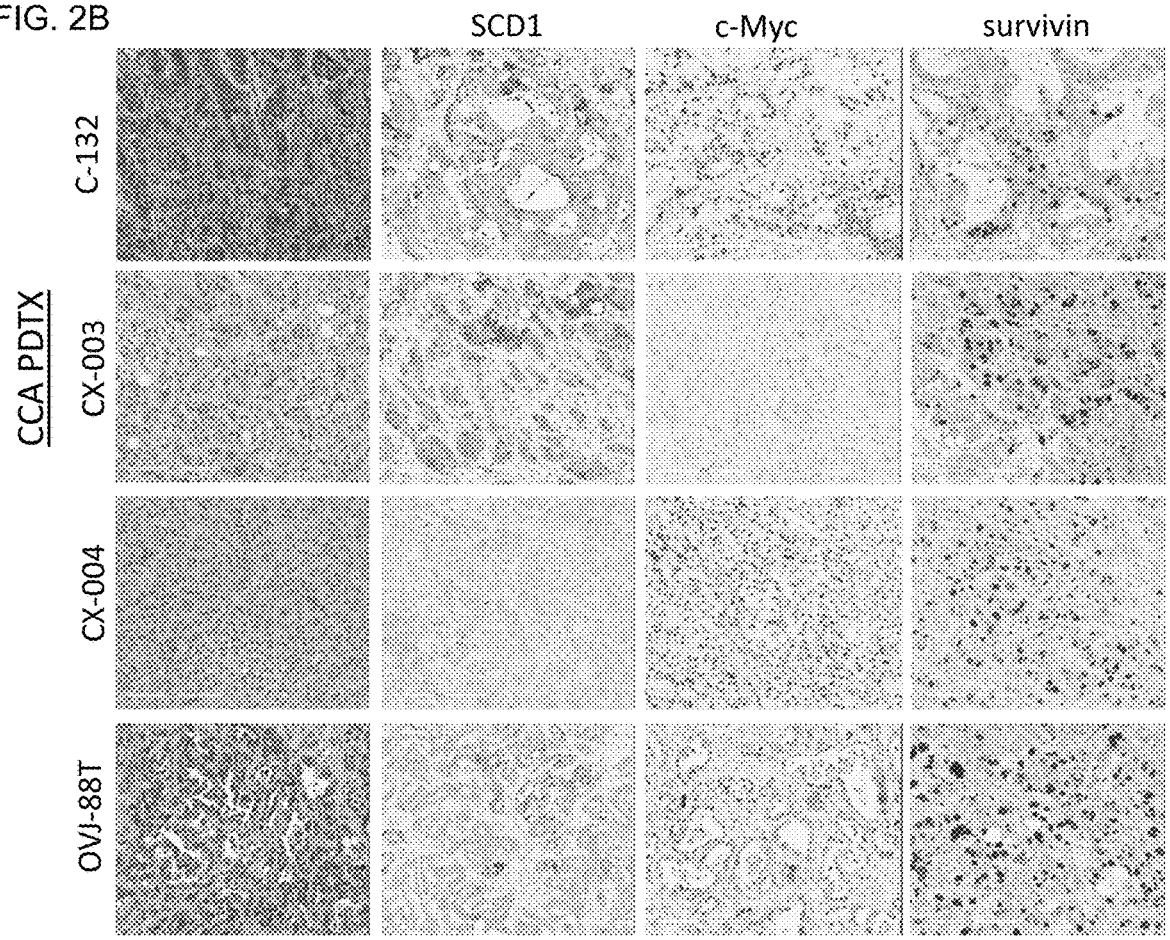

SCD1 protein expression was examined by IHC in HCC and CCA tissues using tissue microarrays comprising of HCC, CCA and normal patient tissues (FIG. 1A). Samples were quantitated as H scores and graphed (FIG. 1B). SCD1, c-Myc and survivin protein expression was also examined by IHC in HCC and CCA PDTX avatar models. All six models expressed SCD1 and survivin while c-Myc was absent only in the CX-003 CCA PDTX model. (FIG. 2A-2B).

Small Molecule SCD1 Inhibitors

Figure 3A:
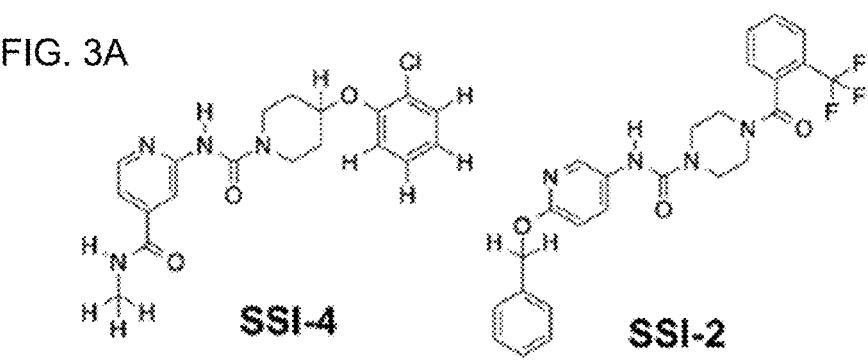
FIGS. 3A-3E shows specificity and oral bioavailability of SCD1 inhibitors.
Figure 3B:
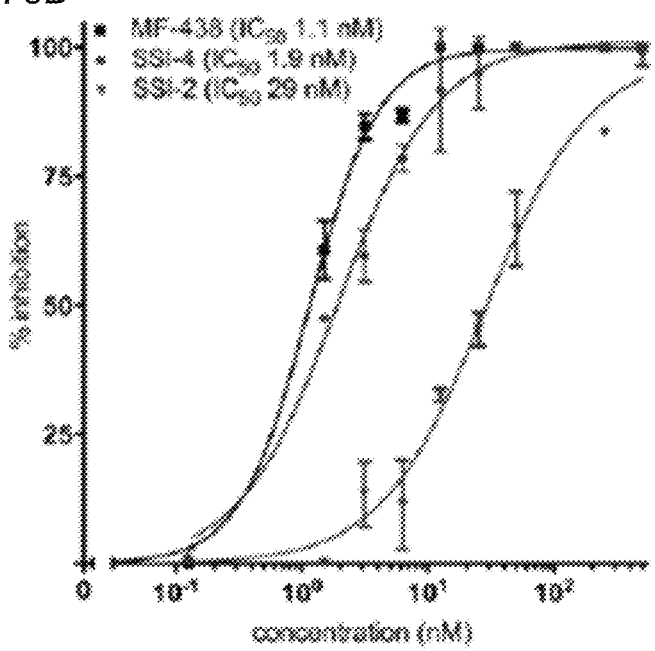
Figure 3C:
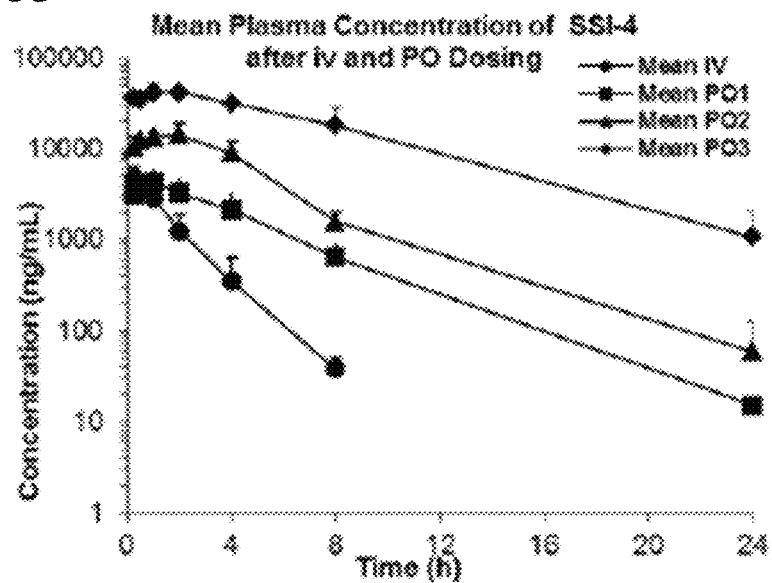
Figures 3D, 3E:
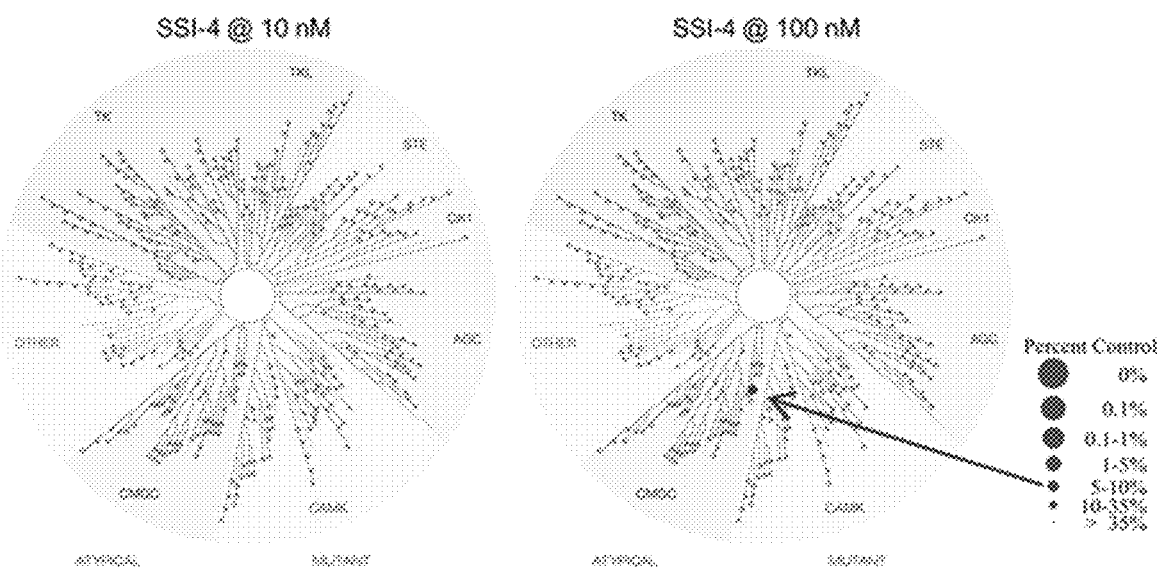
Figure 4A:
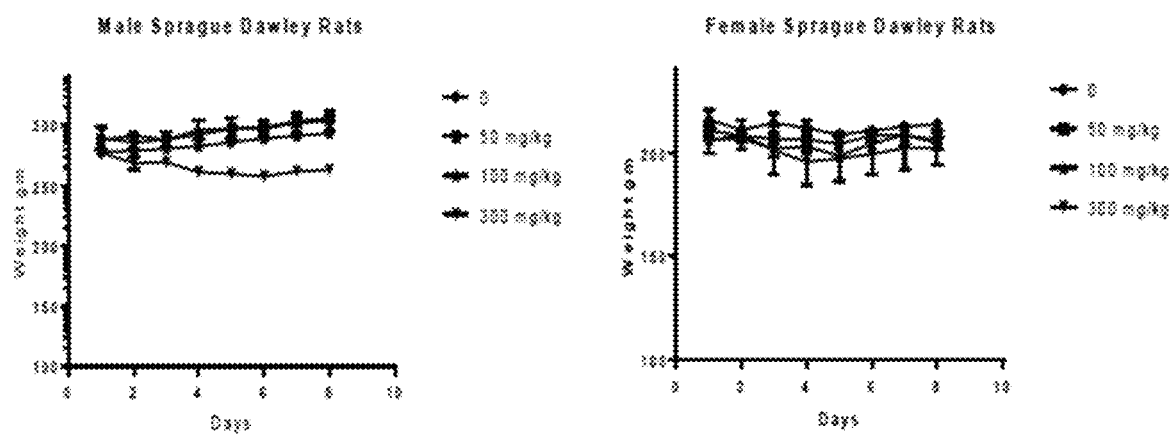
FIGS. 4A-4B show that SSI-4 has a favorable toxicity profile.
Figure 4B:
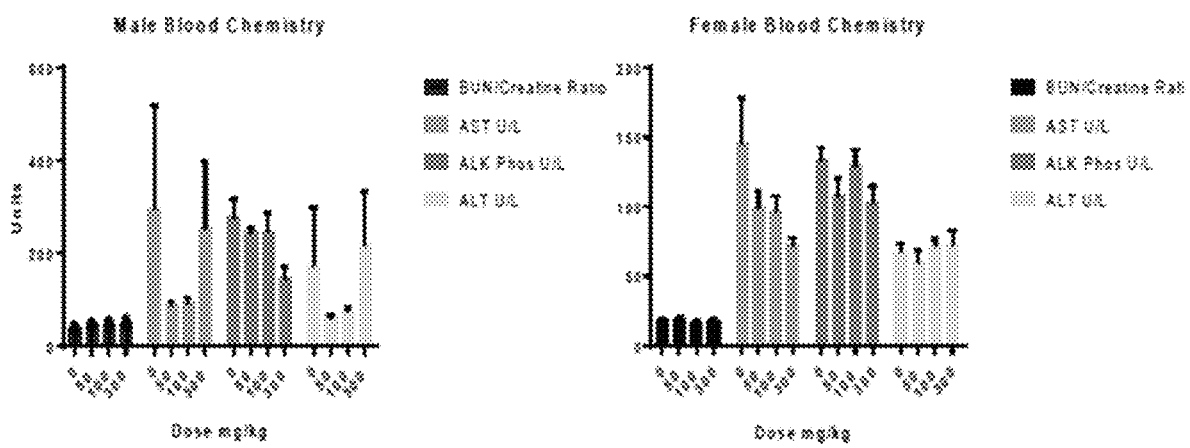

4 SCD1 inhibitors were synthesized with SSI-4 and SSI-2 as the top contenders as shown (FIG. 3A). SCD1 inhibitor SSI-4 demonstrated an IC50 of 1.9 nM related to inhibition of oleoyl CoA biosynthesis by mouse liver microsomes (FIG. 3B). SSI-4 also demonstrated excellent oral bioavailability with a half-life of 3-4 hours following a single oral dose (FIG. 3C). IC50 concentrations for blocking SCD1 enzyme activity and blood half-life and bioavailability of single dose SSI-4 was determined. Half-life and bioavailability information for SSI-4 are shown in FIG. 3D. Bioavailability (%) was calculated with area under the curve ($AUG_{0-last}$) and nominal dose. Half-life in hours of SSI-4 in blood=T½ (h); Dose=D; Maximum concentration=Cmax. On the TREEspot chart for the full matrix SSI-4 kinome scan of 468 kinases, it showed that only 1 weak affinity binding kinase, CDKL2, was observed at 100 nM treatment while none was present at 10 nM indicating no significant off target kinases were affected (FIG. 3E). Toxicity of SSI-4 was examined. Little to no toxicity was seen in male or female rats with minor weight loss (6%) in males at the extremely high dose of 300 mg/kg (FIG. 4A). Blood chemistries were in normal range (FIG. 4B).

In Vitro Effects of the SCD1 Inhibitor, SSI-4

Figure 5A:
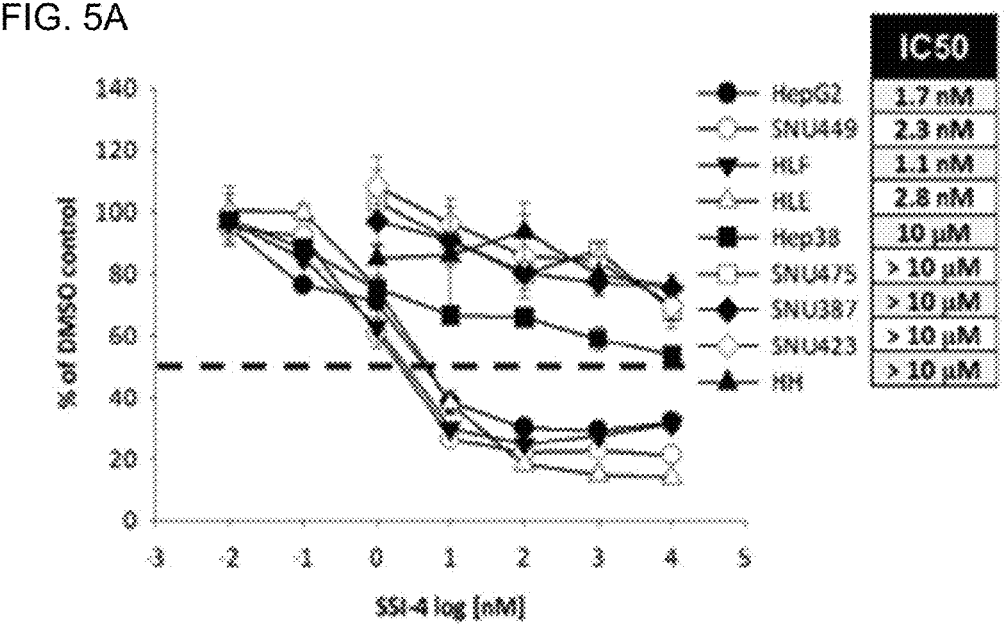
FIGS. 5A-5F show that SSI-4 demonstrated high affinity and specificity for SCD1.
Figure 5B:
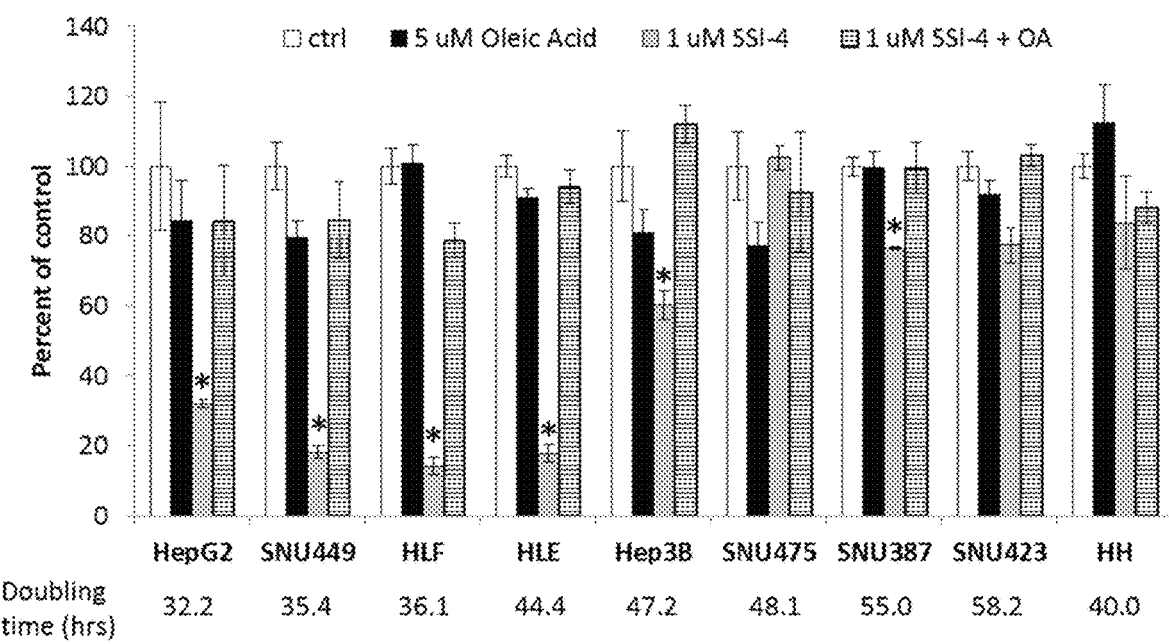
Figure 5C:
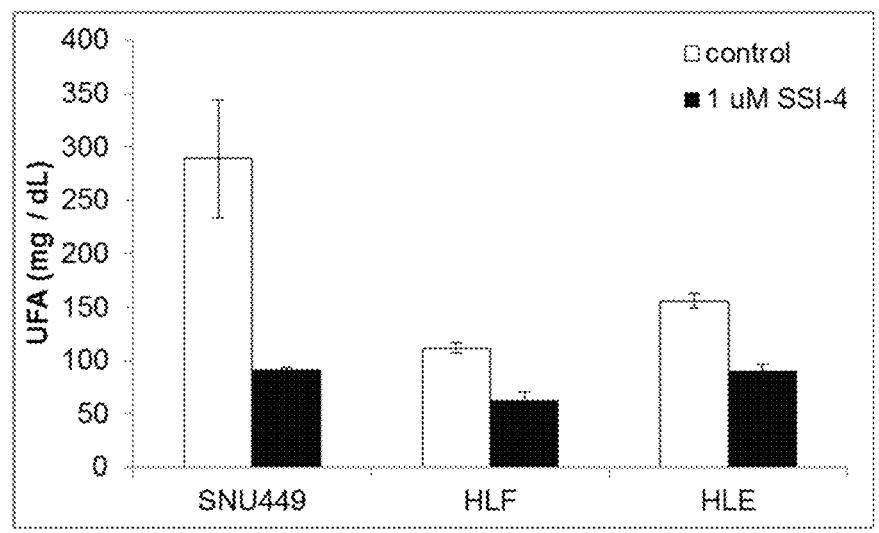
Figure 5D:
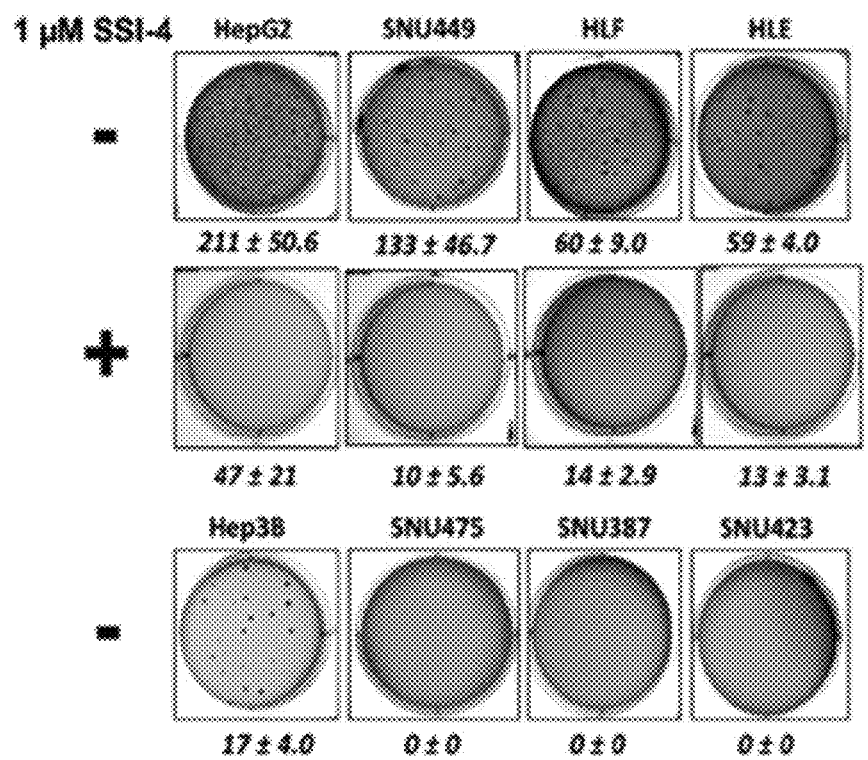
Figure 5E:
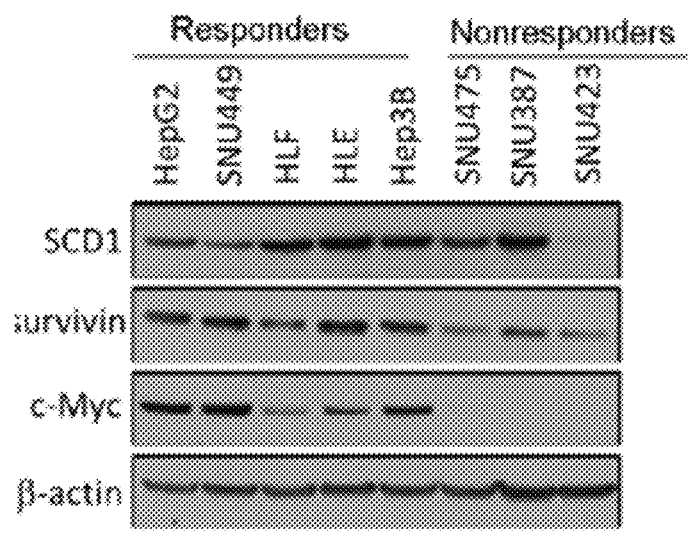
Figure 5F:
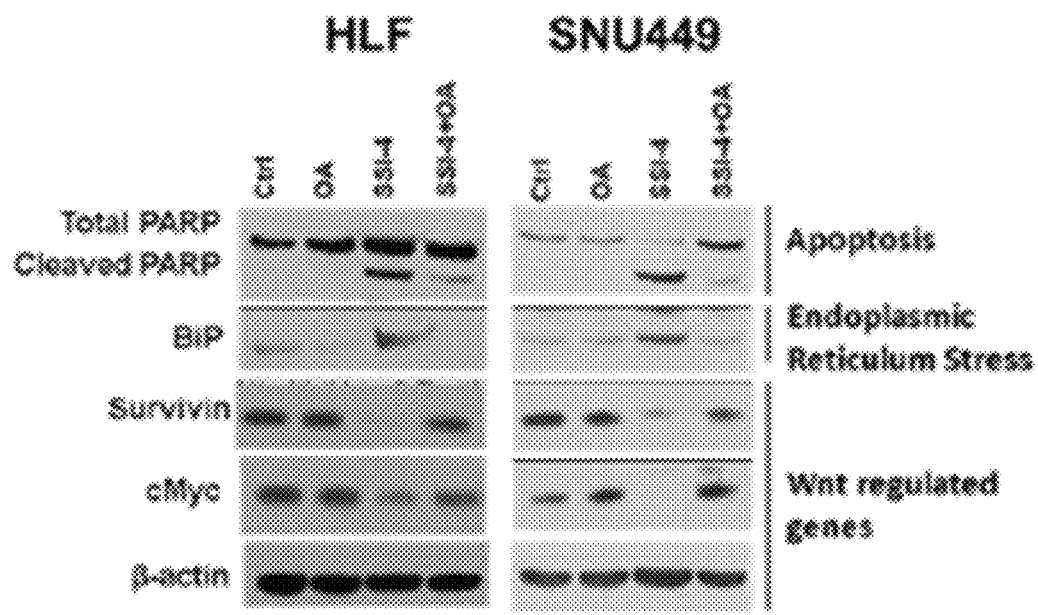
Figure 5G:
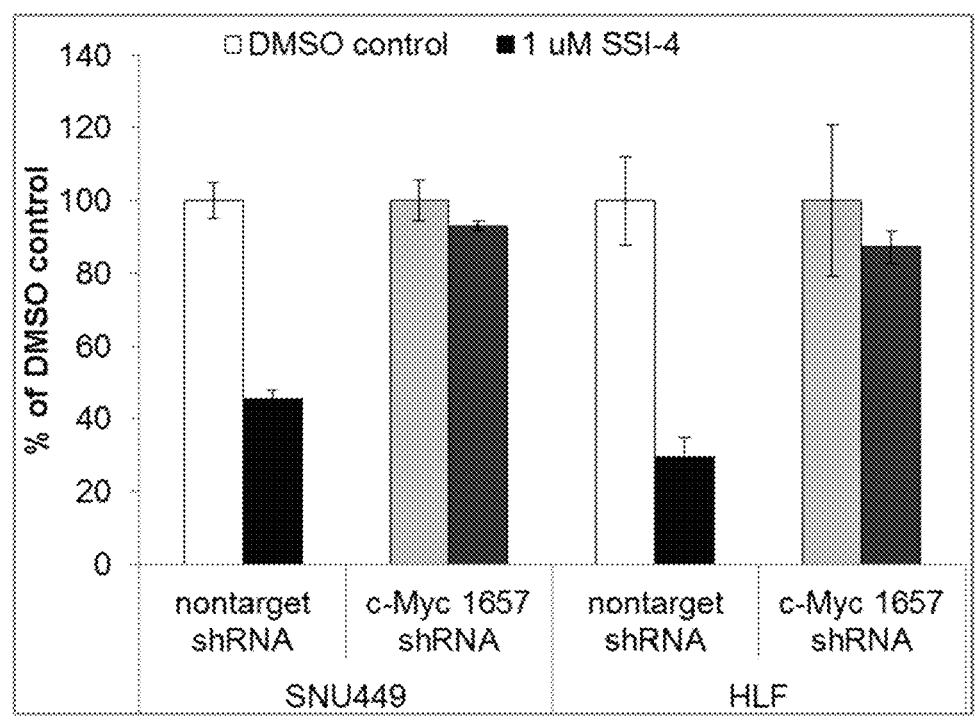
FIG. 5G contains a graph showing cell proliferation of SSI4 responsive HCC cells infected with either a control nontarget shRNA or c-Myc 1657 shRNA with SSI-4 treatment. Addition of 1 uM SSI-4 to cMyc shRNA cells (red) showed no difference from that of cMyc shRNA alone (gray).
Figure 5H:
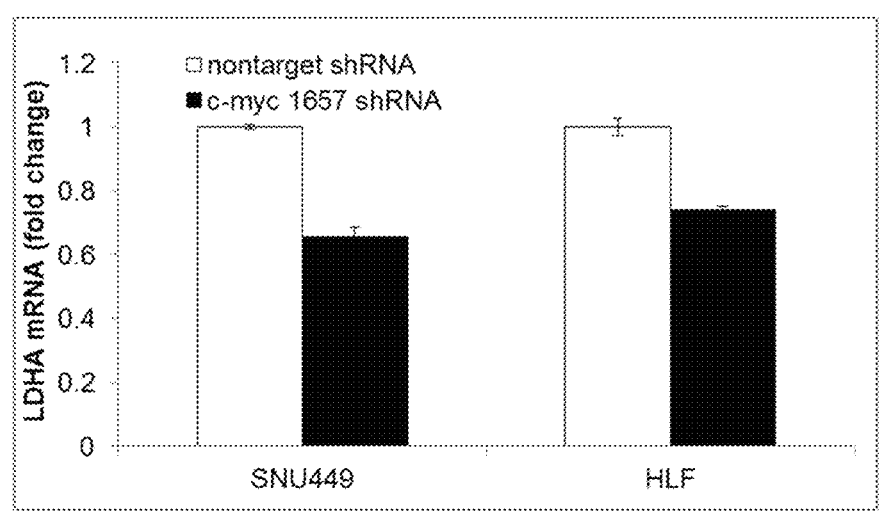
FIG. 5H contains a graph showing LDHA mRNA levels in HCC cells infected with either nontarget shRNA and c-Myc 1657 shRNA. When c-Myc was silenced, LDHA mRNA decreases (black). These data indicated that cMyc, LDHA, and SCD1 are in the same pathway.

Dose out of HCC cell lines show that some lines are highly responsive with IC50's under 5 nM while others are 10 μM or higher (FIG. 5A). Doubling times of responsive cell lines was less than 47 hours versus the non-responsive cell lines indicating that rapidly dividing cells require MUFAs which are incorporated into cell membranes. Oleic acid rescue demonstrated specificity for SCD1. Normal human hepatocytes (HH) cells were not growth inhibited by 1 μM SCD1 (FIG. 5B) demonstrating tumor specificity. Levels of unsaturated fatty acids decreased upon SSI-4 treatment indicating that the conversion of saturated fatty acids to unsaturated fatty acids was being blocked (FIG. 5C). Anchorage-independence was examined via soft agar assays which showed that SSI-4 responsive cells were anchorage-independent (>20 colonies) while SSI-4 nonresponsive cells were anchorage-dependent (<20 colonies). In responsive cells, SSI-4 decreased colony formation (FIG. 5D). Wnt regulated genes, survivin and cMyc, were upregulated at the protein level in SSI-4 responsive cell lines (FIG. 5E). SSI-4 down-regulated Wnt regulated genes (cMyc, survivin and cyclin D1) while inducing apoptosis (cleaved PARP) and ER stress (BIP) (FIG. 5F). HCC cells silenced for cMyc with shRNA showed blunted response to SSI-4, thus, mechanistically linking SCD1 and cMyc to cell proliferation (FIG. 5G). Silencing c-Myc also downregulated LDHA which mechanistically links SCD1 and cMyc to glycolysis (FIG. 5H).

Antitumor Activity of SSI-4

Figure 6A:
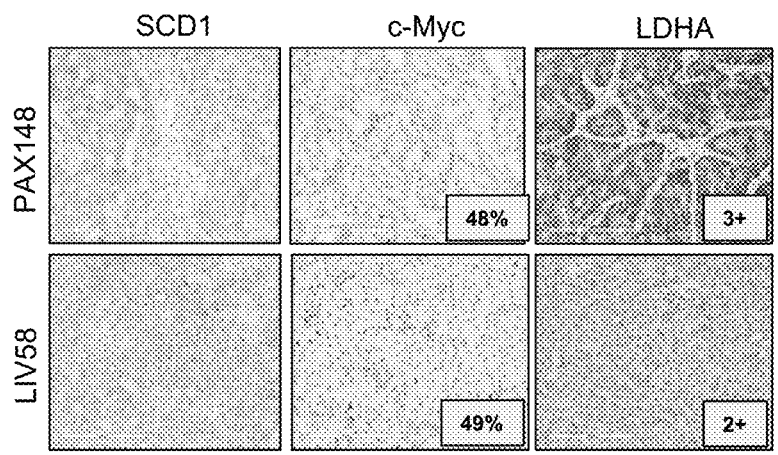
FIGS. 6A-6C show that SCD1 inhibits in vivo HCC cell proliferation and demonstrates synergy with sorafenib.
Figure 6B:
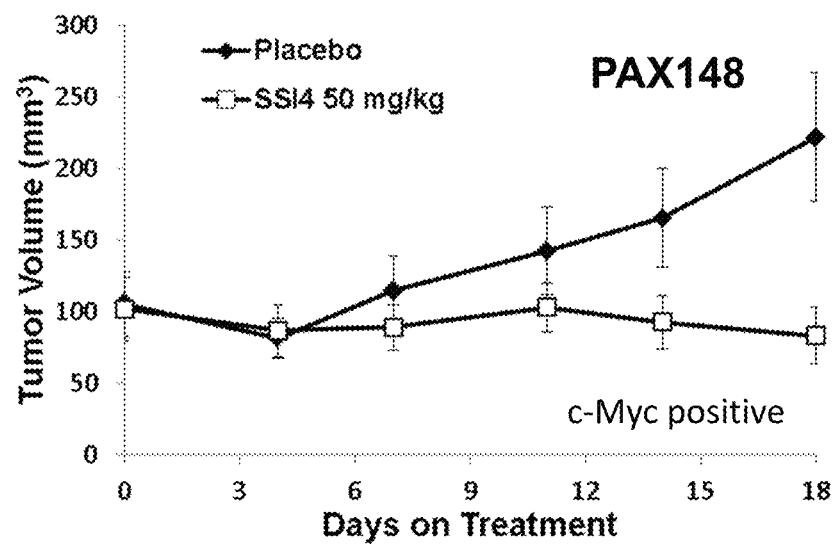
Figure 6C:
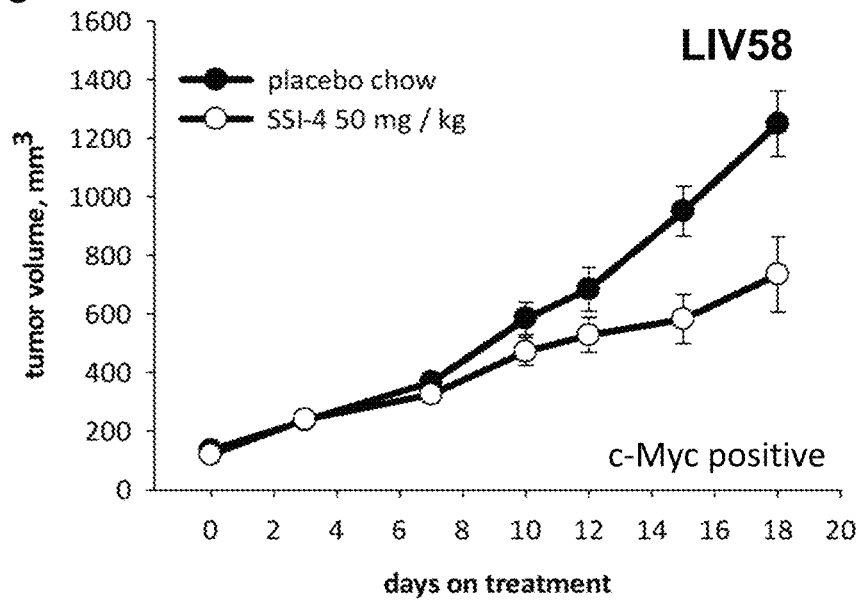
Figure 6D:
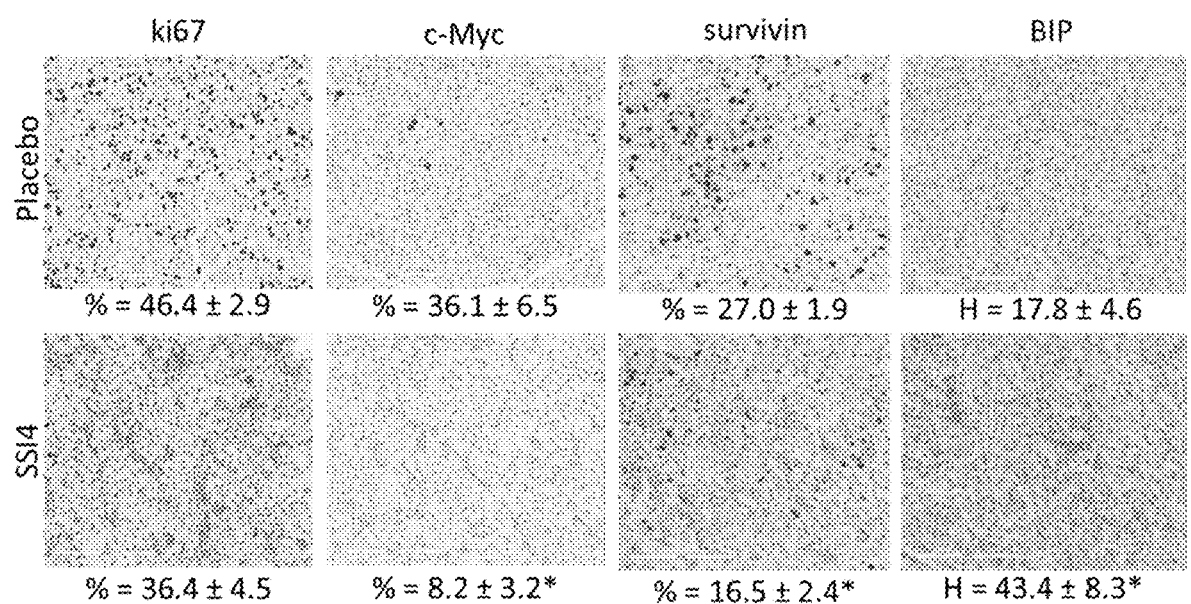
FIG. 6D contains images of IHC detection of Ki-67, cMyc, and survivin proteins expressed in LIV58 tumors treated with control (placebo) or SSI-4. IHC showed that nuclear Ki-67, cMyc, and survivin protein were attenuated in response to SSI-4 in mice. ER stress was induced as evidenced by BIP upregulation. H score is calculated based upon signal intensity (0-3) using the formula: [(1+%×1)+(2+%×2)+(3+%×3)]. * indicates statistical significance (P>0.05).

HCC PDTX models that share equal positivity of SCD1 and c-Myc, have differences in expression for LDHA (FIG. 6A). SSI-4 treatment demonstrated in vivo antitumor activity of SSI-4 in the 2 PDTX models (FIG. 6B-6C). The PAX148 model was highly sensitive and expressed high levels of LDHA while the LIV58 model was ~30% responsive and expressed low levels of LDHA (FIG. 6A-6C). This indicated that SSI-4 response is correlated with metabolic activity. The ability of SCD1 to control the final step of Wnt biological activation via fatty acylation was also examined in LIV58 PDTX mice with attenuated Ki-67, survivin and cMyc along with upregulated BIP, a biomarker of ER stress (FIG. 6D). These results demonstrate that a link between SCD1 inhibition, Wnt-dependent signaling, ER stress and metabolism in both HCC cell culture and PDTX animal models.

SCD1 Inhibitor as a Combinatorial Therapeutic with Sorafenib

Figure 7A:
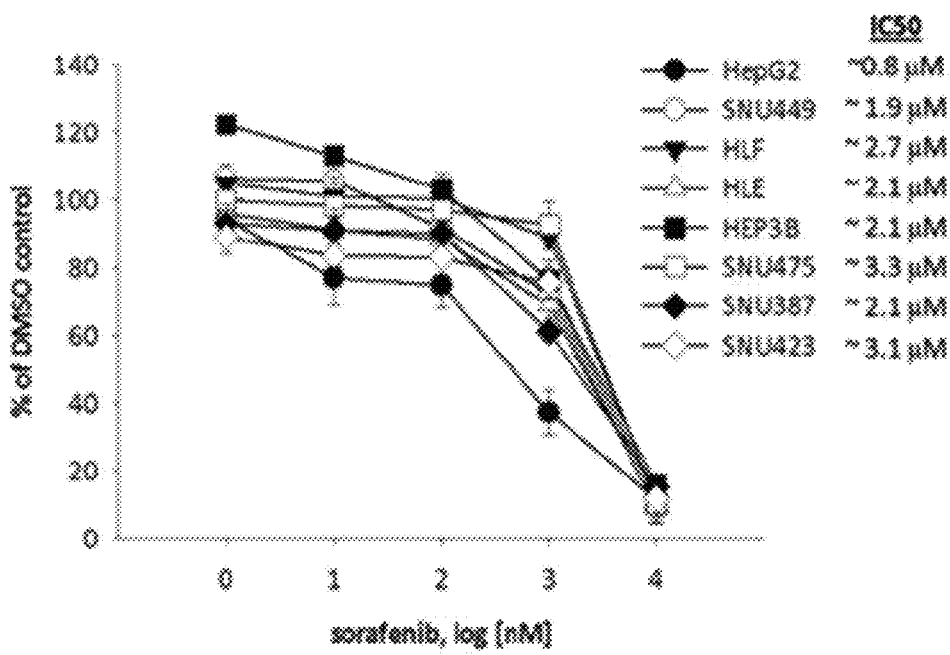
FIGS. 7A-7D show that SSI-4 demonstrated single agent antitumor activity and synergy with sorafenib in HCC models.
Figure 7B:
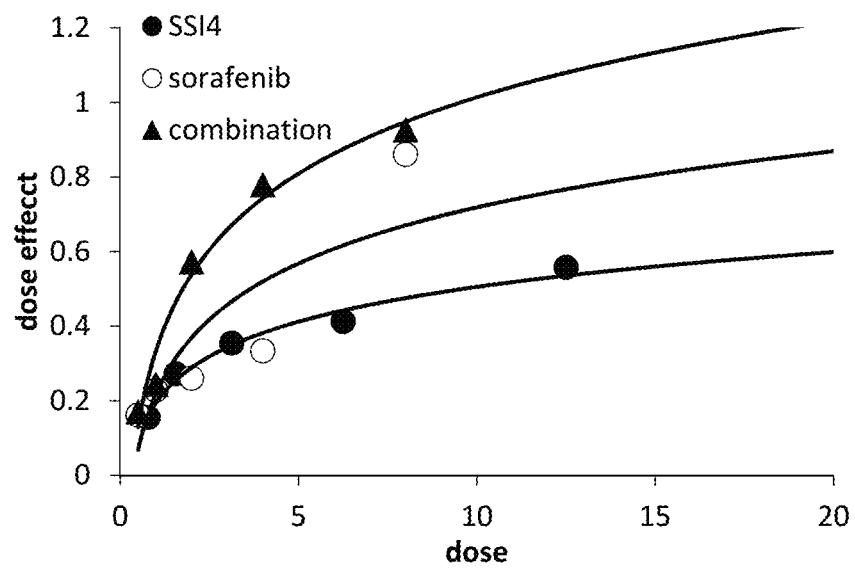
Figure 7C:
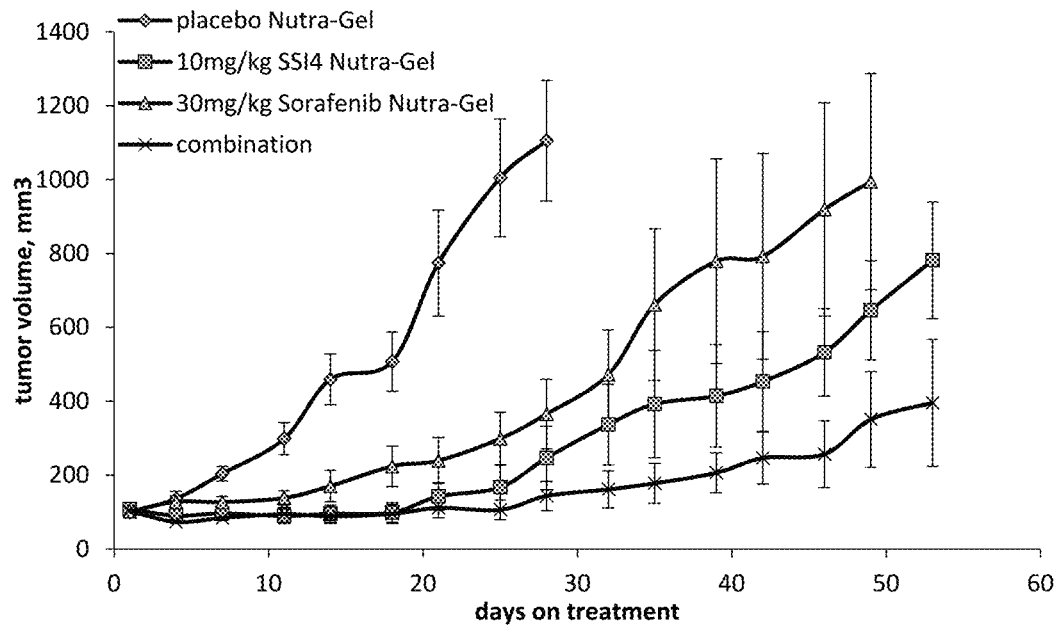
Figure 7D:
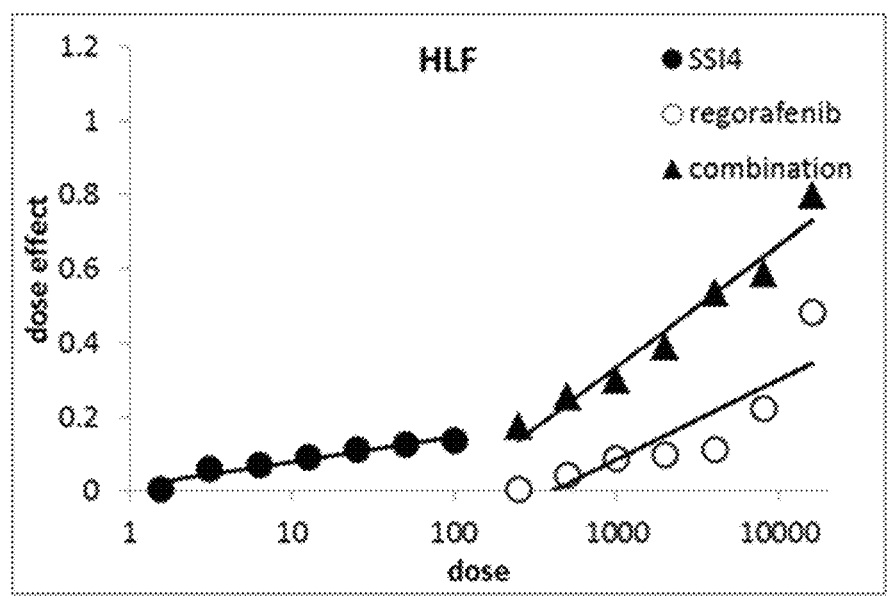

Any synergistic effect of SSI-4 and sorafenib was examined in SNU449 cells. All cell lines tested responded to sorafenib (IC50=1.7-6.4 μM; FIG. 7A). Cell proliferation was analyzed with a combination of SSI-4 plus sorafenib in SNU449 cells (FIG. 7B). Using the method of Chou and Talalay, combination index (CI) was used to determine whether these two compounds when combined act synergistically (<0.8), additively (<1.1>0.8), or antagonistically (>1.1). The CI of all doses of SSI-4 plus 1 μM sorafenib was <0.6 indicating a highly synergistic interaction in inhibiting cell proliferation. The combination of SSI-4 with sorafenib showed in vivo prolonged durable response in a HLE HCC mouse model while single agent sorafenib and SSI-4 escape over time on therapy (FIG. 7C). Regorafenib, an analog of sorafenib, also exhibited synergy when used in combination with SSI-4 in HLF cells based upon the Chou and Talalay method (FIG. 7D).

SSI-4 in CCA Preclinical Models

Figure 8A:
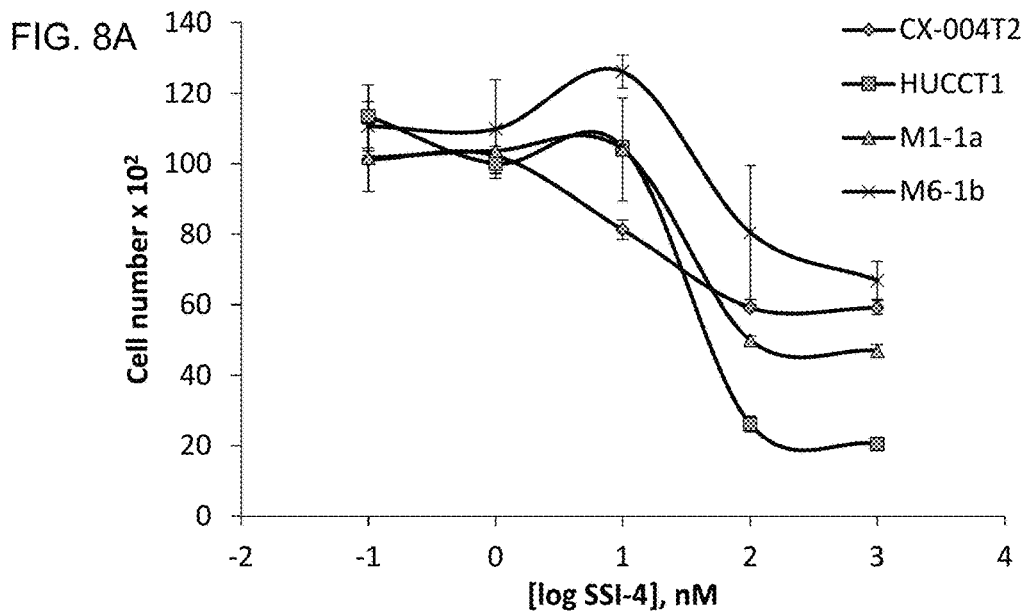
FIGS. 8A-8C show that SCD1 inhibits cell proliferation in human (CX-004T2 and HUCCT1) and mouse (M1-1a and M6-1b) cholangiocarcinoma (CCA) cell lines.
Figure 8B:
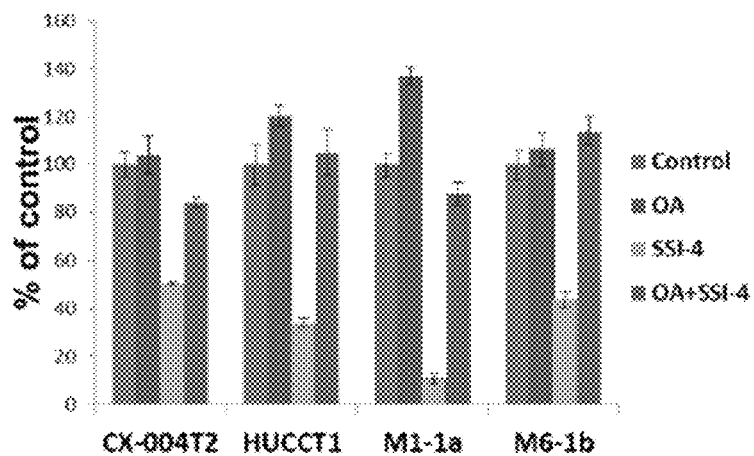
Figure 8C:
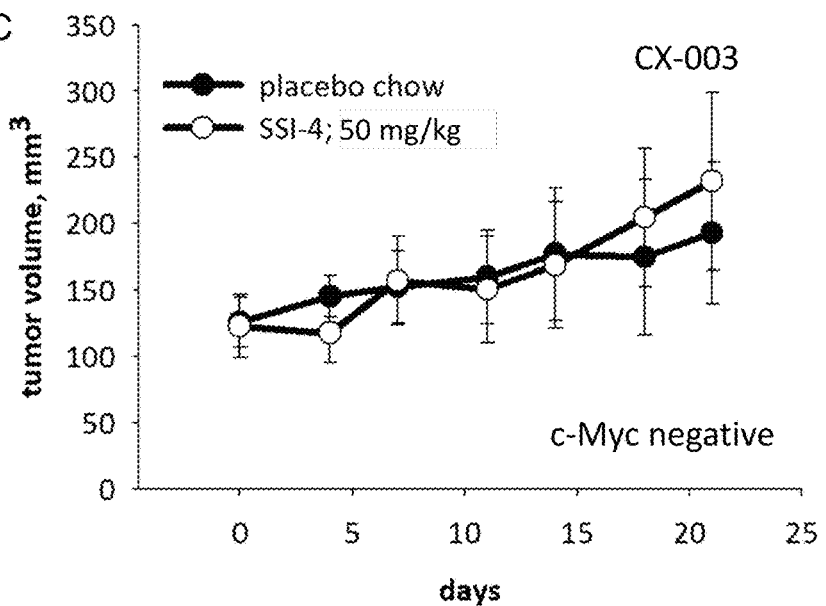

Antitumor effects of SSI-4 were also examined for CCA. Human and mouse CCA cell lines demonstrated growth inhibition when treated with SSI-4 (FIG. 8A). Oleic acid rescued the growth inhibitory effect of SSI-4 (FIG. 8B). Using a CCA PDTX model that was c-Myc negative, in vivo results showed no response to SSI-4; thus, SSI-4 response is only observed in c-Myc driven tumors (FIG. 8C).

CONCLUSIONS

These results demonstrate that SCD1-associated cancers that overexpress Wnt regulated polypeptides are responsive to SSI-4 and that SSI-4, alone or in combination with sorafenib, can be used to provide effective therapy for aggressive HCC.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying and treating a mammal having a cancer exhibiting stearoyl-Coenzyme A desaturase 1 (SCD1) polypeptide expression that is responsive to treatment with a SCD1 polypeptide inhibitor, said method comprising:

detecting an elevated level of cMyc polypeptides within a biological sample of cancer from said mammal, thereby identifying said cancer as being responsive to treatment with said SCD1 polypeptide inhibitor, and administering said SCD1 polypeptide inhibitor to said mammal, wherein said SCD1 polypeptide inhibitor is a compound having Formula (II) or Formula (IIa):

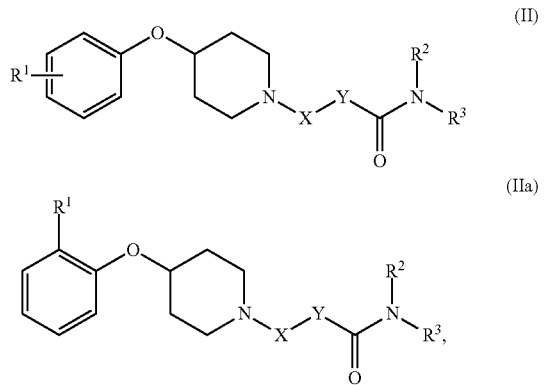

or pharmaceutically acceptable salt thereof;
wherein:
$R^1$ is halo;
X is $(C=O)NR^4$—;

Y is

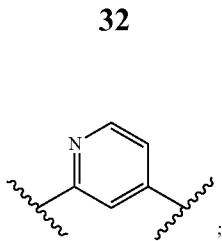

and
$R^2$, $R^3$, and $R^4$ are each independently H or an unsubstituted $C_{1-6}$alkyl.

2. The method of claim 1, wherein said SCD1 polypeptide inhibitor is SSI-4, 2-{[4-(2-Chlorophenoxy)piperidine-1-carbonyl]amino}-N-methylpyridine-4-carboxamide:

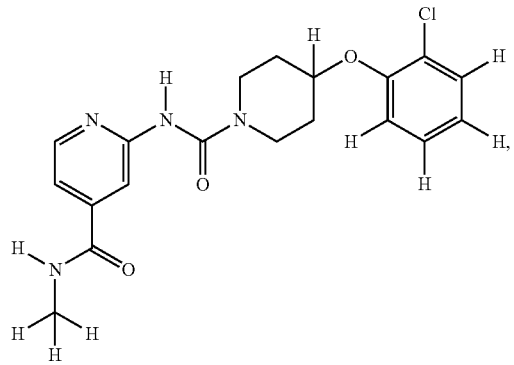

or pharmaceutically acceptable salt thereof.

3. The method of claim 1, wherein said method comprises detecting SCD1 polypeptide expression within said biological sample.

4. The method of claim 1, wherein said mammal is a human.

5. The method of claim 1, wherein said cancer is selected from the group consisting of liver cancer, renal cell carcinoma, ovarian cancer, breast cancer, prostate cancer, colon cancer, pancreatic cancer, bladder cancer, lung cancer, thyroid cancer, brain cancer, melanoma, and lymphoma.

6. The method of claim 5, wherein said cancer is a liver cancer.

7. The method of claim 6, wherein said liver cancer is a hepatocellular carcinoma.

8. The method of claim 6, wherein said liver cancer is a cholangiocarcinoma.

9. The method of claim 1, further comprising detecting an elevated level of survivin polypeptides within said biological sample from said mammal.

10. The method of claim 1, wherein said method further comprises administering an additional therapeutic agent used to treat cancer to said mammal.

11. The method of claim 10, wherein said additional therapeutic agent is a chemotherapeutic agent.

12. The method of claim 11, wherein said chemotherapeutic agent is a kinase inhibitor.

13. The method of claim 12, wherein said kinase inhibitor is selected from the group consisting of sorafenib, regorafenib, bortezomib, erlotinib, gefitinib, imatinib, vemurafenib, and vismodegib.

14. The method of claim 13, wherein said kinase inhibitor is sorafenib.

* * * * *